(12) United States Patent
Straus et al.

(10) Patent No.: US 9,574,234 B2
(45) Date of Patent: *Feb. 21, 2017

(54) SOLID-PHASE CLONAL AMPLIFICATION AND RELATED METHODS

(71) Applicant: Illumina, Inc., San Diego, CA (US)

(72) Inventors: Neil A. Straus, Emeryville, CA (US); Shengrong Lin, Fremont, CA (US); Helmy A. Eltoukhy, Atherton, CA (US); Kevin L. Gunderson, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 2 days.

This patent is subject to a terminal disclaimer.

(21) Appl. No.: 14/593,902

(22) Filed: Jan. 9, 2015

(65) Prior Publication Data
US 2015/0141295 A1 May 21, 2015

Related U.S. Application Data

(63) Continuation of application No. 13/637,770, filed as application No. PCT/US2011/028644 on Mar. 16, 2011, now Pat. No. 8,951,940.

(60) Provisional application No. 61/320,250, filed on Apr. 1, 2010.

(51) Int. Cl.
*C12Q 1/68* (2006.01)

(52) U.S. Cl.
CPC ........... *C12Q 1/6874* (2013.01); *C12Q 1/6834* (2013.01); *C12Q 1/6837* (2013.01); *C12Q 2531/125* (2013.01); *C12Q 2563/149* (2013.01)

(58) Field of Classification Search
None
See application file for complete search history.

(56) References Cited

U.S. PATENT DOCUMENTS

| 6,133,436 | A | 10/2000 | Koster et al. |
| 8,951,940 | B2 * | 2/2015 | Straus ............ C12Q 1/6834 435/6.1 |
| 2008/0242560 | A1 | 10/2008 | Gunderson et al. |
| 2009/0018024 | A1 | 1/2009 | Church et al. |
| 2009/0062129 | A1 | 3/2009 | McKernan et al. |

FOREIGN PATENT DOCUMENTS

WO 2006/138257 12/2006

OTHER PUBLICATIONS

Dunning, "Beadarray: classes and methods for Illumine bead-based data", Bioinformatics, vol. 23, No. 16, 2007, 2183-2184.
(Continued)

*Primary Examiner* — Betty Forman

(57) ABSTRACT

The present invention provides methods and compositions for analyzing nucleic acid sequences. In some aspects, the methods utilize clonal objects, such as DNA balls, that have been captured on beads. Using the methods described here, compositions are fabricated wherein a bead and one clonal object are affinity bound or hybridized to each other through an affinity binding patch or hybridization patch on the surface of the bead. The invention also provides a population of beads having affinity bound or hybridized clonal objects at a ratio of 1:1. The invention additionally provides methods for amplifying a target nucleic acid molecule utilizing the compositions described herein.

17 Claims, 10 Drawing Sheets

(56) References Cited

OTHER PUBLICATIONS

Gunderson, et al., "Decoding randomly ordered DNA arrays", Genome Research, 14, 2004, 870-877.
International Search Report, "Application No. PCT/US2011/028644", mailed Apr. 11, 2013.
Sato, et al., "Microbead-based rolling circle amplification in a microchip for sensitive DNA detection", Lab on a chip, 10(10), 2010, 1262.

* cited by examiner

US 9,574,234 B2

SOLID-PHASE CLONAL AMPLIFICATION AND RELATED METHODS

FIELD OF THE INVENTION

The present invention relates generally to compositions and methods for analyzing nucleic acid sequences, and more specifically to compositions having a solid substrate and a clonal object for analysis including methods of fabricating and using the compositions.

BACKGROUND OF THE INVENTION

The task of cataloguing human genetic variation and correlating this variation with susceptibility to disease is daunting and expensive. A single genome sequence has a price tag of approximately $50,000. A drastic reduction in this cost is imperative for advancing the understanding of health and disease. The near term goal in genomics analysis is to resequence the human genome at a cost of approximately $1,000 dollars. A reduction in sequencing costs will require a number of technical advances in the field. Fortunately, the same basic principles of readout parallelization and sample multiplexing that proved so powerful for gene expression and SNP genotyping analysis are also being successfully applied to large-scale sequencing. Technical advances that could reduce the cost of genome analysis include: (1) library generation; (2) highly-parallel clonal amplification and analysis; (3) development of robust cycle sequencing biochemistry; (4) development of ultrafast imaging technology; and (5) development of algorithms for sequence assembly from short reads.

The ability to specify the content of the DNA library in a targeted manner is extremely useful for a number of applications. In particular, the ability to resequence all exons in the cancer genome would greatly facilitate the discovery of new cancer genes. The comprehensive resequencing of cancer genomes is a major objective of the Cancer Genome Atlas Project (cancergenome.nih.gov/index.asp) and would greatly benefit from a reduction in sequencing price. Unfortunately, creating a targeted library of the 250,000 exons from the genome is cumbersome using current methods. The approach of single-plex PCR for each exon is clearly cost prohibitive. As such, parallelization of the sample preparation is of paramount importance in reducing sequencing costs.

In addition to library generation, the creation of clonal amplifications in a highly-parallel manner is also important for cost-effective sequencing. Sequencing is generally performed on clonal populations of DNA molecules traditionally prepared from plasmids grown from picking individual bacterial colonies. In the human genome project, each clone was individually picked, grown-up, and the DNA extracted or amplified out of the clone. In recent years, there have been a number of innovations to enable highly-parallelized analysis of DNA clones particularly using array-based approaches. In the simplest approach, the library can be analyzed at the single molecule level which by its very nature is clonal. The major advantage of single molecule sequencing is that cyclic sequencing can occur asynchronously since each molecule is read out individually. In contrast, analysis of clonal amplifications requires near quantitative completion of each sequencing cycle, otherwise background noise progressively grows with each ensuing cycle severely limiting read length. As such, clonal analysis places a bigger burden on the robustness of the sequencing biochemistry and may potentially limit read lengths.

Thus, there exists a need to develop methods to improve genomics analysis and provide more cost effective methods for sequence analysis. The present invention satisfies this need and provides related advantages as well.

SUMMARY OF THE INVENTION

The present invention provides methods and compositions for analyzing nucleic acid sequences. In some embodiments, the methods utilize clonal objects, such as DNA balls, that have been captured on beads. Embodiments of the invention provide compositions having a bead and one clonal object, wherein the clonal object is affinity bound or hybridized to the bead, for example, through patch on the surface of the bead, such as an affinity binding patch or a hybridization patch. In some aspects, the patch includes a plurality of polynucleotides attached to a single region on the surface of the bead. Embodiments of the invention also provide a population of beads having affinity bound or hybridized clonal objects. In particular embodiments, each of the clonal objects are affinity bound or hybridized to the beads through a patch on the surface of each bead, such as an affinity binding patch or a hybridization patch. The ratio of beads to bound or hybridized clonal objects in the population can be 1:1. In particular embodiments, no more than one clonal object is bound or hybridized to any given bead in the population.

Using the methods described herein, compositions can be fabricated wherein a bead and one clonal object are affinity bound or hybridized to each other through attachment to a patch on the surface of the bead. Embodiments of the invention can provide a method of fabricating an affinity binding patch on a bead by providing a bead having a plurality of capture moieties; providing a solid surface having a plurality of capture-complement moieties, wherein the capture-complement moieties further comprise a cleavable moiety and an affinity ligand; specifically binding the capture moieties to the capture-complement moieties, thereby forming an immobilized bead on the solid surface; and cleaving the cleavable moiety so as to retain the affinity ligand on the bead, thereby fabricating an affinity binding patch on the bead. In particular embodiments, the capture moieties or the capture-complement moieties or both include capture sequences of polynucleotides. Accordingly, embodiments of the invention can provide a method of fabricating an affinity binding patch on a bead by providing a bead having a plurality of first polynucleotides attached to the surface of the bead, wherein the first polynucleotides each have a capture sequence; providing a solid surface having a plurality of second polynucleotides attached to the solid surface, wherein the second polynucleotides each have a capture-complement sequence, a cleavable moiety and an affinity ligand; hybridizing the capture sequences of the first polynucleotides to the capture-complement sequences of the second polynucleotides, thereby forming an immobilized bead on the solid surface; and cleaving the second polynucleotides at the cleavable moiety so as to retain the affinity ligand on the second plurality of polynucleotides, thereby fabricating an affinity binding patch on the bead. In some aspects, the method further includes fabricating one clonal object bound to the affinity binding patch by contacting the affinity ligand with a binding agent, wherein the binding agent has two or more binding sites, and binding one clonal object to the binding agent through a second affinity ligand on the clonal object, wherein the one clonal object has a single tandemly repeated target nucleic acid molecule, thereby fabricating one clonal object bound to the affinity binding patch.

Embodiments of the invention can provide a method of fabricating a bead having one clonal object by providing a bead having a plurality of first capture moieties; providing a solid surface having a plurality of second capture moieties patterned into patches on the surface, wherein the second capture moieties each have a cleavable moiety, wherein one clonal object is bound to one patch on the surface via one or more of the second capture moieties, wherein the one clonal object has a single tandemly repeated target nucleic acid molecule; specifically binding the first capture moiety to the clonal object, thereby forming an immobilized bead on the solid surface, and cleaving the cleavable moiety so as to retain the clonal object, thereby fabricating a bead having one clonal object. In particular embodiments, the capture moieties comprise polynucleotides. Accordingly, embodiments of the invention can provide a method of fabricating a bead having one clonal object by providing a bead having a plurality of first polynucleotides; providing a solid surface having a plurality of second polynucleotides patterned into patches on the surface, wherein the second polynucleotides each have a cleavable moiety, wherein one clonal object is hybridized to one polynucleotide patch on the surface, wherein the one clonal object has a single tandemly repeated target nucleic acid molecule; hybridizing the first polynucleotides to the clonal object, thereby forming an immobilized bead on the solid surface, and cleaving the second polynucleotides at the cleavable moiety so as to retain the clonal object, thereby fabricating a bead having one clonal object.

Embodiments of the invention can provide a method of fabricating a hybridization patch on a bead by providing a bead having a plurality of first polynucleotides attached to the surface of the bead, wherein the first polynucleotides each have a first capture sequence, providing a solid surface having a plurality of second polynucleotides attached to the solid surface, wherein the second polynucleotides each have a first capture-complement sequence and a second capture-complement sequence, hybridizing the first capture sequences of the first polynucleotides to the first capture-complement sequence of the second polynucleotides, thereby forming an immobilized bead on the solid surface, and extending the first polynucleotides of the immobilized bead using the second capture-complement sequence as a template, thereby fabricating a hybridization patch of extended first polynucleotides on the bead, the extended first polynucleotides having a second capture sequence. In some aspects, the method further includes fabricating one clonal object bound to the patch on the bead by providing a clonal object having the second capture-complement sequence, and hybridizing the second capture-complement sequence of the clonal object to the second capture sequences of the bead, thereby fabricating one clonal object bound to the patch on the bead. In some aspects of the method, extending the first polynucleotides includes the addition of one or more nucleoside triphosphates having an affinity ligand, thereby fabricating an affinity binding patch on the bead.

The invention additionally provides methods of amplifying a target nucleic acid molecule utilizing the compositions described herein. Embodiments of the invention provide a method of amplifying a target nucleic acid molecule by placing the compositions or populations of beads having affinity bound or hybridized clonal objects described herein onto a solid surface having microwells, wherein only one bead can spatially fit into one microwell and amplifying the target nucleic acid molecules in the microwells, thereby forming amplicons. In some aspects, the method further includes sequencing the amplified target nucleic acid molecules using methods such as sequencing by synthesis, sequencing by ligation or sequencing by hybridization, thereby determining the nucleic acid sequence of the target nucleic acid molecule.

BRIEF DESCRIPTION OF THE DRAWINGS

The figures are intended to illustrate broad concepts of the invention by reference to representative examples for ease of discussion. They are not intended to limit the scope of the invention by showing one out of several alternate embodiments or by showing or omitting optional features of the invention.

DETAILED DESCRIPTION OF THE INVENTION

Figure 1:
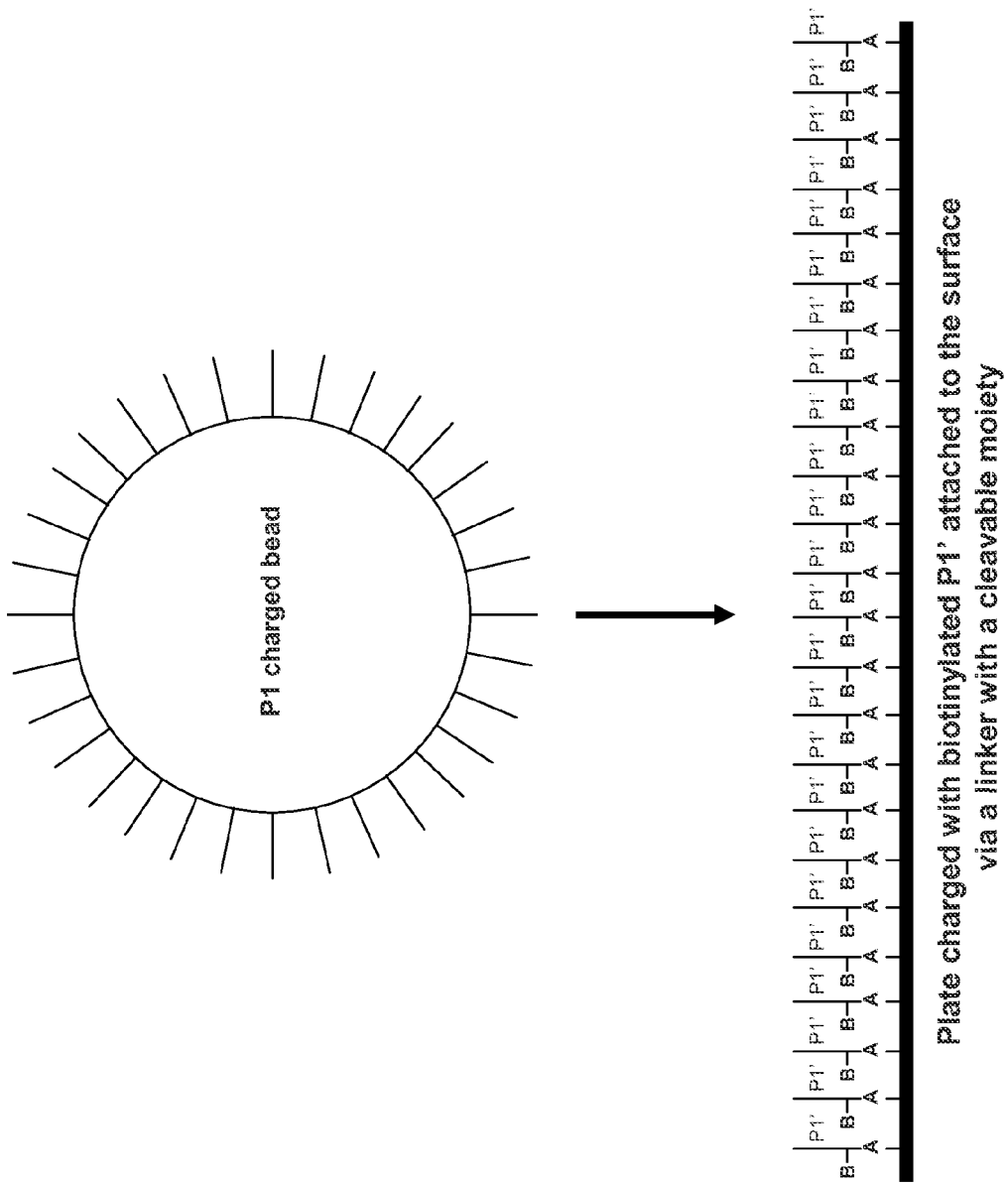
FIG. 1 shows a schematic depiction of a bead charged with (P1) primer polynucleotides for hybridization to a plate having complementary biotinylated (P1') primer polynucleotides attached to the solid surface by a linker having a cleavable moiety. (B) represents the affinity ligand biotin. (A) represents the linker having a cleavable moiety.

In some embodiments, the present invention provides methods and compositions for analyzing nucleic acid sequences. Embodiments of the invention provide compositions having a bead and one clonal object, wherein the clonal object is affinity bound or hybridized to the bead through a patch on the surface of the beads, wherein the patch includes a plurality of polynucleotides attached to a single region on the surface of the bead. Embodiments of the invention also provide a population of beads having affinity bound or hybridized clonal objects, wherein each of the clonal objects are affinity bound or hybridized to the beads through a patch on the surface of each of the beads, wherein the patch includes a plurality of polynucleotides attached to a single region on the surface of the beads and wherein the ratio of beads to bound or hybridized clonal objects is 1:1.

In some aspects of the invention, the clonal object has a single tandemly repeated target nucleic acid molecule. Such clonal objects include, for example, DNA balls, particles formed of or with nucleic acids, circular library elements and the like generated using methods described herein or using any method known to one of skill in the art. Accordingly, embodiments of the invention provide a composition having a bead and one clonal object, wherein the one clonal object includes a single tandemly repeated target nucleic acid molecule and said clonal object is affinity bound or hybridized to the bead through a patch on the surface of the bead, wherein the patch includes a plurality of polynucleotides attached to a single region on the surface of the bead. Embodiments of the invention also provide a population of beads having affinity bound or hybridized clonal objects, wherein each of the clonal objects includes a single tandemly repeated target nucleic acid molecule and each of the clonal objects being affinity bound or hybridized to the beads through a patch on the surface of each bead, wherein the patch includes a plurality of polynucleotides attached to a single region on the surface of the beads and wherein the ratio of beads to bound or hybridized clonal objects is 1:1. In some aspects, the invention also provide that the patch on the bead or on each bead of a population can be a defined area of sufficient size that limits the number of clonal objects that can bind or hybridize to the bead. For example, in some aspects of the invention, the patch on the surface of the bead is less than 1000 nm$^2$, or alternatively less than 500 nm$^2$, or alternatively less than 100 nm$^2$.

In accordance with particular embodiments of the invention, beads can be fabricated to have a patch on the surface that has reactivity, binding affinity or other characteristics that differ from the rest of the surface of the bead. The patch can be created by selectively modifying the area on the surface of the bead that comes into contact with a solid surface. As set forth in further detail below, the patch can be created to have one or more affinity ligands so as to create an affinity binding patch on the bead. In some embodiments, the affinity ligand can be transferred from a solid surface to a surface of the bead. For example, the affinity ligand can be a ligand or receptor that is attached to a nucleic acid that is in turn attached to the solid surface via a cleavable linker and transfer can occur via hybridization of the nucleic acid to a complementary sequence on the bead, followed by cleavage from the solid phase surface. In some embodiments, the solid surface, or a chemical attached thereto, can participate in transfer of an affinity ligand from solution to the surface of the bead. For example, the affinity ligand can be a nucleic acid capture sequence that is encoded by a capture complement sequence present in a solid-surface-attached polynucleotide. In this example, a bead-bound polynucleotide can be hybridized to the solid-surface-attached polynucleotide and the bead-bound polynucleotide can be extended (for example, by a polymerase or ligase) using the capture complement sequence as a template such that the bead-bound nucleic acid will acquire the capture sequence. In a similar method, the bead-bound polynucleotide can be extended to incorporate nucleotides or oligonucleotides that have an affinity ligand (such as biotin). In further exemplary embodiments, a solid surface, or a chemical attached thereto, can react with a reactant on the surface of the bead to synthesize an affinity ligand on the bead, or the solid surface, or a chemical attached thereto, can expose or deprotect an affinity ligand on the surface of the bead.

Beads having an affinity binding patch can be useful for creating a clonal library of target nucleic acids. The affinity binding patch allows efficient creation of a collection of beads in which each bead carries a single target nucleic acid sequence (whether the single sequence is present in a single copy or multiple copies) and in which few or no beads are devoid of a target nucleic acid sequence. As exemplified in several embodiments below, a population of target nucleic acids can be contacted with beads under conditions wherein only a single target nucleic acid is capable of binding to the affinity patch such that no more than one target nucleic acid is attached to any given bead. For example, the target nucleic acids can be in the form of clonal objects, such as DNA balls or nucleic acids in particle form, that individually bind to a patch so as to sterically exclude subsequent clonal objects from binding to the same patch. Since only a single target nucleic acid is capable of binding to any bead, saturating amounts of target nucleic acid can be contacted with the beads to drive the reaction toward yielding a population of beads in which most or all of the individual beads have an attached target nucleic acid. This ability to drive the reaction to a state in which few to no beads lack a target nucleic acid (i.e. "blank" beads) provides advantages over other methods that rely on limiting amounts of nucleic acid to yield a Poisson distribution of beads bearing a single target nucleic acid because the latter methods, although yielding few beads with more than one target nucleic acid, end up having a large number of blank beads. In many embodiments blank beads are undesirable since they can consume time and resources in downstream analyses. A clonal library created using the methods set forth herein can provide separation of individual sequences and efficient use of beads to provide benefits for multiplex analyses of complex nucleic acid samples such as genomes. Several exemplary applications including nucleic acid analysis as set forth in further detail below.

The terms "microsphere" and "bead" are used interchangeably and mean a small body made of a rigid or semi-rigid material. The body can have a shape characterized, for example, as a sphere, oval, microsphere, or other recognized particle shape whether having regular or irregular dimensions. In particular embodiments the small body has a curved surface. Populations of microspheres or other small bodies can be used for attachment of populations of capture probes, amplicons, DNA balls or other nucleic acids. The composition of a microsphere can vary, depending for example, on the format, chemistry and/or method of attachment and/or on the method of nucleic acid synthesis. Exemplary microsphere compositions include solid supports, and chemical functionalities imparted thereto, used in polypeptide, polynucleotide and/or organic moiety synthesis. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as any other materials which can be found described in, for example, "*Microsphere Detection Guide*" from Bangs Laboratories, Fishers Ind., which is incorporated herein by reference. The sizes of the microsphere or bead that can be useful for the methods described herein can be determined by one of skill in the art and include, without limitation, about 1 µm, about 2 µm, about 3 µm, about 5 µm, about 10 µm, about 20 µm, about 30 µm, about 40 µm, about 60 µm, about 100 µm, about 150 µm or about 200 µm in diameter. Other particles can be used in ways similar to those described herein for beads and microspheres.

A "patch" refers to a small piece, portion or section of a surface to which one or a plurality of things are attached or hybridized. A patch can also be referred to by the type of thing that is attached or hybridized to the surface. For example, an affinity binding patch refers to a patch that includes an affinity binding ligand to which a corresponding binding agent can bind or pair. As another example, a hybridization patch refers to a patch that includes a polynucleotide or nucleic acid molecule that can hybridize to another polynucleotide or nucleic acid molecule.

In some aspects of the invention, a patch on the surface of a microsphere or bead can contain a plurality of polynucleotides attached to a single region the surface of the microsphere or bead. In some aspects of the invention, a patch can also contain an affinity ligand or binding agent. In some aspects of the invention, the area of a patch is less than the area of the surface of the microsphere or bead. The configuration of the patch can have any of a variety of shapes or contours. For example, the surface of the patch can be generally planar or curved. In some aspects, the patch is of sufficient size as to allow binding of only one clonal object per region. Such a size determination will depend on the size of the microsphere or bead, the length of polynucleotides attached thereto and the size and/or composition of the clonal object. The shape of the patch is also not limited and will depend on the shape of the microsphere or bead itself and the method used to generate the region containing the polynucleotides. The patch can be a contiguous area on a surface that excludes another area on the surface. The excluded area can partially surround the patch or, alternatively, the excluded area can entirely surround the patch. Non-limiting examples of the size of the patch described herein include a contiguous area of less than 1000 nm$^2$, or alternatively less than 900 nm$^2$, or alternatively less than 800 nm$^2$, or alternatively less than 700 nm$^2$, or alternatively less than 600 nm$^2$, or alternatively less than 500 nm$^2$, or alternatively less than 400 nm$^2$, or alternatively less than 300 nm$^2$, or alternatively less than 200 nm$^2$, or alternatively less than 100 nm$^2$, or alternatively less than 50 nm$^2$. Additionally, the size of the patch described herein can be a percentage of the overall surface area of the bead, for example, the size of the patch can be a contiguous area that is no more than 0.001%, or alternatively no more than 0.005%, or alternatively no more than 0.01%, or alternatively no more than 0.05%, or alternatively no more than 0.1%, or alternatively no more than 0.5%, or alternatively no more than 1.0%, or alternatively no more than 2%, or alternatively no more than 5%, or alternatively no more than 10% or alternative no more than 20%, or alternatively no more than 30%, or alternatively no more than 40%, or alternatively no more than 50% of the surface area of the bead.

In particular embodiments, a patch can include a surface to which a plurality of things are attached or hybridized. Such things can include, but are not limited to, nucleic acids, polynucleotides, oligonucleotides, probes, target molecules, proteins, ligands, receptors, capture moieties, capture-complement moieties or any of a variety of other molecules set forth herein or otherwise known in the art. It will be understood that the surface within a patch need not necessarily be entirely occupied by those things, and those things can be present at any of a variety of quantities, surface densities or local concentrations within the patch. Typically, an area on a surface that is excluded from a patch will be devoid of one or more types of things that are attached to the surface within the patch.

In some aspects of the invention, a plurality of polynucleotides on a bead or on each bead of a population include a universal primer sequence, a nucleic acid sequence fully or partially complementary to the polynucleotides attached to a solid surface or a target nucleic acid molecule. In some aspects, the plurality of polynucleotides on the bead or on each bead of a population have a sufficient length which allows for immobilization on a solid surface having complementary polynucleotides or hybridization to a clonal object. Exemplary lengths include, without limitation, 10, 20, 30, 40, 50, 60, 70, 80, 90, 100, 150, 200, 300, 400 or 500 or more nucleotides. In some aspects, the polynucleotide length is at least 10 nucleotides, but no more than 1000, 900, 800, 700, 600, 500, 400, 300, 200, 150, 100, 90, 80, 70, 60, 50, 40, 30, or 20 nucleotides. The invention also provides that lengths in between these exemplified sizes can also be sued in the compositions and methods of the invention.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), genomic DNA, genomic DNA fragment, exon, intron, messenger RNA (mRNA), transfer RNA, ribosomal RNA, ribozyme, cDNA, recombinant polynucleotide, branched polynucleotide, plasmid, vector, isolated DNA of any sequence, isolated RNA of any sequence, nucleic acid probe, primer or amplified copy of any of the foregoing. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that makes or uses a polynucleotide encompasses both the double-stranded form and each of two complementary single-stranded forms known or predicted to make up the double-stranded form. Unless otherwise specified or required, a "copy" of a polynucleotide can include the exact copy of the polynucleotide and the complementary copy of the polynucleotide in single or double stranded form. In some aspects of the invention, the lengths of the plurality of polynucleotides on a bead or solid support are at least 10, 20, 30, 40, 50, 60, 70, 80, 90, 100, 150, 200, 300, 400 or 500 or more nucleotides. Alternatively or additionally, the lengths are no more than 1000, 900, 800, 700, 600, 500, 400, 300, 200, 150, 100, 90, 80, 70, 60, 50, 40, 30 or 20 nucleotides.

In some aspects of the compositions or methods described herein, the polynucleotides on a bead or solid support have a "capture sequence". A "capture sequence" refers to a stretch of nucleotides which when hybridized to a complementary nucleotide sequence present on a polynucleotide or clonal object gains control of or becomes associated with any attached molecule, such as a bead or solid surface. The capture sequence can be continuous or non-continuous and will depend on the a number of variables including, but not limited to, the size of the attached molecule, the location of the capture sequence within the polynucleotide and the hybridization methods used. A sequence having sufficient complementarity to a capture sequence to allow specific hybridization is referred to herein as a "capture-complement sequence." In particular embodiments, the capture-complement sequence includes a sequence that is perfectly complementary to the capture sequence. The length of the capture sequence and/or the capture-complement sequence can be at least 10, 20, 30, 40, 50, 60, 70, 80, 90, 100, 150, 200, 300, 400 or 500 or more nucleotides. Alternatively or additionally, the lengths are no more than 1000, 900, 800, 700, 600, 500, 400, 300, 200, 150, 100, 90, 80, 70, 60, 50, 40, 30 or 20 nucleotides. Capture sequences and capture-complement sequences are examples of capture moieties and capture-complement moieties, respectively. Capture sequences and capture complement sequences can also function as affinity ligands. Although several embodiments of the invention are exemplified herein with respect to capture sequences and capture-complement sequences, it will be understood that other moieties can be used such as affinity ligands set forth elsewhere herein or other moieties known in the art that are capable of specific binding interactions.

A polynucleotide can be composed of a specific sequence of four nucleotide bases: adenine (A); cytosine (C); guanine (G); and thymine (T). Uracil (U) can also be present, for example, as a natural replacement for thymine when the polynucleotide is RNA. Uracil can also be used in DNA. Thus, the term "polynucleotide sequence" is the alphabetical representation of a polynucleotide molecule. This alphabetical representation can be input into databases in a computer having a central processing unit and used for bioinformatics applications such as functional genomics, sequence alignment, sequence building and homology searching.

A nucleic acid used in the invention can also include native or non-native bases. In this regard a native deoxyribonucleic acid can have one or more bases selected from the group consisting of adenine, thymine, cytosine or guanine and a ribonucleic acid can have one or more bases selected from the group consisting of uracil, adenine, cytosine or guanine. It will be understood that a deoxyribonucleic acid used in the methods or compositions set forth herein can include uracil bases and a ribonucleic acid can include a thymine base. Exemplary non-native bases that can be included in a nucleic acid, whether having a native backbone or analog structure, include, without limitation, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. A particular embodiment can utilize isocytosine and isoguanine in a nucleic acid in order to reduce non-specific hybridization, as generally described in U.S. Pat. No. 5,681,702.

A non-native base used in a nucleic acid of the invention can have universal base pairing activity, wherein it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which basepairs with cytosine, adenine or uracil. Non-native bases can be modified to include a peptide-linked label. The peptide can be attached to the base using methods exemplified herein with regard to native bases. Those skilled in the art will know or be able to determine appropriate methods for attaching peptides based on the reactivities of these bases. Alternatively or additionally, oligonucleotides, nucleotides or nucleosides including the above-described non-native bases can further include reversible blocking groups on the 2', 3' or 4' hydroxyl of the sugar moiety.

As used herein, a "universal sequence" refers to a sequence that can be attached, for example, by ligation or other methods disclosed herein, to a nucleic acid sequence, particularly in a population of nucleic acid molecules, such that the same sequence is attached to a plurality of different nucleic acid molecules. As used herein, a "plurality" refers to two or more. Such a universal sequence is therefore "common" to the many different nucleic acid molecules to which it is attached. Such a universal sequence is particularly useful for analyzing multiple samples simultaneously, as disclosed herein. Examples of universal sequences are universal primers and universal priming sites. A universal priming site contains a "common priming site" to which an appropriate primer can bind to and which can be utilized as a priming site for synthesis of nucleic acid sequences complementary to the nucleic acid sequence attached to the universal primer.

A primer sequence can be described as "universal" when the same primer sequence appears among a plurality or even all of the polypeptides, so that a small set of primers can be used for amplification of many or all of the target nucleic acid molecules in the same reaction. The universal priming sequence can be, for example, between 15 and 30 nucleotides in length in some embodiments, and between 17 and 20 nucleotides in other embodiments.

In some aspects of the invention, a plurality of polynucleotides on a bead or on each bead of a population, include one or more affinity ligands attached to the polynucleotides. Non-limiting examples of affinity ligands useful in the invention are biotin, imino-biotin, an antibody or functional fragment thereof, an aptamer, a Spiegelmer, a receptor, avidin, streptavidin, neutravidin, a nucleic acid, a peptide or a peptide nucleic acid. Methods of attaching an affinity ligand to the plurality of polynucleotides will depend on the affinity ligand being used, the location of the affinity ligand on the polynucleotide, i.e. 5' and 3' ends or within the polynucleotides, and the point of attachment on the polynucleotide, i.e. the sugar backbone, phosphate group or base. Methods for attaching an affinity ligand to a polynucleotide are well know to one skilled in the art. One example includes incorporation of biotinylated nucleotides by terminal deoxynucleotidyl transferase or using DNA polymerase (Flickinger et al., *Nucleic Acids Research* Vol. 20(9):2382 (1992) and Tabor and Boyle, *Curr. Protoc. Immunol.* Chapter 10:Unit 10.10). Biotinylated dNTPs are commercially available from a number of sources including (Life Technologies—Carlsbad, Calif.) and (Roche Diagnositcs Corporation—Indianapolis, Ind.). Another example of attaching an affinity ligand to a polynucleotide includes induction of cross-linkages of polynucleotide-proteins by ultraviolet irradiation (Budowsky et al., *European Journal of Biochemistry* 159(1):95-101 (1986)). It is also possible to use a primer having one or more affinity ligands such that the products of an extension or amplification reaction using the primer will include the one or more affinity ligands.

In some aspects of the invention, the affinity ligands attached to the polynucleotides are capable of binding to one or more binding agent. Non-limiting examples of binding agents useful in the invention include avidin, streptavidin, neutravidin, biotin, imino-biotin, an antibody or functional fragment thereof, an aptamer, a Spiegelmer, a receptor, a nucleic acid, a peptide and a peptide nucleic acid. A particularly useful binding agent is streptavidin, a tetrameric protein with a biotin binding-site in each monomeric unit, which makes it capable of binding to one, two, three or four biotin molecules. Other binding agents having two or more binding sites for a ligand of interest are also particularly useful.

The term "affinity" refers to how tightly a ligand, such as a chemical compound, binds to a binding agent, such as a protein. The affinity between a ligand and a binding agent can often be expressed by the dissociation constant between the ligand and the binding agent. The ligand-binding agent affinities can be influenced by a number of different interactions such as non-covalent intermolecular interactions including, but not limited to, hydrogen bonding, electrostatic interactions, hydrophobicity and Van der Waals forces. Exemplary ligand-binding agent pairs that can be used in the invention include, but are not limited to, immunoglobulins (i.e. antibodies) or functional fragments thereof (i.e. Fab, $F(ab)_2$ Fv, and single chain Fv (scFv)) and antigen (i.e. protein or peptide); biotin and avidin or analogues thereof having specificity for avidin, such as imino-biotin, or having specificity for biotin, such as streptavidin or neutravidin; peptide and peptide interactions, such as a ligand and a receptor; peptide nucleic acids (PNA) and nucleic acids, such as DNA or RNA; and carbohydrates and lectins. The binding pairs set forth above can also be used to attach clonal objects such as DNA balls to beads.

The term "hybridized" or "hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. Hybridization reactions can also be performed under "physiological conditions" which is well known to one of skill in the art. A non-limiting example of a physiological condition is the temperature, ionic strength, pH and concentration of Mg+ normally found in a cell.

When hybridization occurs in an antiparallel configuration between two single-stranded polynucleotides, the reaction is called "annealing" and those polynucleotides are described as "complementary". A double-stranded polynucleotide can be complementary or homologous to another polynucleotide, if hybridization can occur between one of the strands of the first polynucleotide and the second. Complementarity or homology (the degree that one polynucleotide is complementary with another) is quantifiable in terms of the proportion of bases in opposing strands that are expected to form hydrogen bonding with each other, according to generally accepted base-pairing rules.

As used herein a "binding agent" refers to a molecule that is capable of binding to one or more affinity ligands as described herein. A binding agent can be attached to a polynucleotide to allow detection or isolation of the nucleic acid via specific affinity to an affinity ligand. A binding agent can be a sequence or sequence region of the polynucleotide. Specific affinity between two binding partners is understood to mean preferential binding of one partner to another compared to binding of the partner to other components or contaminants in the system. Binding partners that are specifically bound typically remain bound under the detection or separation conditions described herein, including wash steps to remove non-specific binding. Depending upon the particular binding conditions used, the dissociation constants of the pair can be, for example, less than about $10^{-6}$, $10^{-7}$, $10^{-8}$, $10^{-9}$, $10^{-10}$, $10^{-11}$, $10^{-12}$, $10^{-13}$, or $10^{-14}$ M.

A further example of a nucleic acid with an analog structure that is useful in the invention is a peptide nucleic acid (PNA). The backbone of a PNA is substantially non-ionic under neutral conditions, in contrast to the highly charged phosphodiester backbone of naturally occurring nucleic acids. This provides two non-limiting advantages. First, the PNA backbone exhibits improved hybridization kinetics. Secondly, PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This can provide for better sequence discrimination. Similarly, due to their non-ionic nature, hybridization of the bases attached to these backbones is relatively insensitive to salt concentration. A PNA or monomer unit used to synthesize PNA can include a base having a peptide linked label. In such cases, an enzyme used to cleave the peptide linker will generally be unreactive toward the PNA backbone.

In some aspects of the invention, a clonal object that is affinity bound or hybridized to a bead or each bead of a population is composed of a single tandemly repeated target nucleic acid molecule, such as, but not limited to, a DNA ball, a circular library element or the like. Methods for generating such clonal objects are well known to one skilled in the art and include the methods described herein such as rolling circle amplification and DNA ligation. The clonal objects of the invention can include multiple copies of the tandemly repeated target nucleic acid molecule. Multiple copies of the target nucleic acid can be useful for certain aspects of sequence analysis, such as providing sufficient starting material for clonal amplification, which in turn allows for a clear signal above any detectable background during sequencing. In some aspects of the invention, the clonal object includes at least 100, or alternatively at least 200, or alternatively at least 500, or alternatively at least 1000, or alternatively at least 2000, or alternatively at least 3000, or alternatively at least 4000, or alternatively at least 5000, or alternatively at least 6000, or alternatively at least 7000, or alternatively at least 8000, or alternatively at least 9000 or alternatively at least 10,000 copies of the target nucleic acid molecule.

It is understood that the size of the clonal object can be affected by the length of the target nucleic acid molecule, the number of copies of the target nucleic acid molecule, the presence or absence of intervening primer, probe or endonuclease recognition sequences and the environmental conditions, which can affect the compaction of the clonal object. Accordingly, in some aspects of the invention, the size of the clonal object is relative to the size of the affinity patch on the surface of the bead or each bead of a population. In other words, in order to attach a single clonal object to a bead, the size of the clonal object is such that once bound to a patch of polynucleotides on the bead, another clonal object is excluded from binding to the bead. For example, the diameter or width of the clonal object can be larger than the diameter or width of the patch on surface of the bead. For example, a clonal object can have a diameter that is larger than 10%, 20%, 30%, 40%, 50%, 60%, 70%, 80%, 90%, 100% or more of the diameter of the patch on the surface of the bead. In some embodiments the diameter of the clonal object can be within a range that is smaller than the diameter of the patch but large enough to exclude binding of a second clonal object of similar size. Exemplary ranges include at least about 50%, 100%, 200%, 400% or 500% of the diameter of the patch.

In some aspects of the invention, the size of the bead is relative to the size of the clonal object, such as, the diameter or width of the bead is equal to the diameter or with of the clonal object. Alternatively, the diameter or width of the bead is larger than the diameter or width of the clonal object, such as, at least 10%, or alternatively at least 20%, or alternatively at least 50%, or alternatively at least 75%, or alternatively at least 100%, or alternatively at least 2 time or alternatively at least 5 times, or alternatively at least 10 times, or alternatively at least 100 times or alternatively at least 500 times, or alternatively at least 1000 times, or alternatively at least 5,000 times larger. In some aspects of the invention, the clonal object has a diameter of 0.1 µm, or alternatively 0.2 µm, or alternatively 0.5 µm, or alternatively 1 µm, or alternatively 2 µm, or alternatively 3 µm, or alternatively 4 µm, or alternatively 5 µm.

As used herein, the term "clonal object" refers to a particle having a nucleic acid sequence in one or more copies. An exemplary clonal object is a nucleic acid that as been amplified from a target nucleic acid molecule and in some aspects has a single tandemly repeated sequence of the target nucleic acid molecule. Such tandemly repeated sequences may also be separated with non-target nucleic acids, such as primer binding sites, endonuclease recognition sites, nucleotides linked to affinity ligands or the like. In particular embodiments a clonal object can be a DNA ball, for example, formed by rolling circle amplification. Methods of generating a clonal object are well known to one of skill in the art and exemplary methods are also described herein. As used herein, a "clonal object" can be synthesized using an amplification technique and thus is also referred to herein as an amplicon. Accordingly, an amplicon is the nucleic acid product of an amplification reaction.

A method for generating an array of amplified nucleic acid sequences can include the step of attaching at least one second universal primer having a second common priming site to a plurality of sample nucleic acid molecules, thereby attaching a first universal primer and a second universal primer to a sample nucleic acid molecule of the plurality of sample nucleic acid molecules. In a particular embodiment, the first universal primer and the second universal primer can be attached to respective ends of each nucleic acid in the plurality of sample nucleic acid molecules by ligation.

In embodiments that include ligation of a first double stranded nucleic acid end to a second double stranded nucleic acid end, the ends to be ligated can be blunt or can have complementary single stranded overhangs. The use of complementary overhangs generally provides an added measure of specificity over blunt end methods because conditions can be used in which non-complementary sequences will not ligate. Further specificity can be attained by partially filling in one overhang end to make it complementary to another end. This fill in method can be used to disfavor unwanted ligation between nucleic acids in a sample that were generated with the same restriction enzyme.

An amplicon typically contains multiple, tandem copies of the circularized nucleic acid molecule of the corresponding sample nucleic acid. That is, each amplicon contains multiple, tandem copies of a single sample nucleic acid molecule, which was circularized. The number of copies can be varied by appropriate modification of the amplification reaction including, for example, varying the number of amplification cycles run, using polymerases of varying processivity in the amplification reaction and/or varying the length of time that the amplification reaction is run, as well as modification of other conditions known in the art to influence amplification yield. Generally, the number of copies of a nucleic acid in an amplicon is at least 100, 200, 500, 1000, 2000, 3000, 4000, 5000, 6000, 7000, 8000, 9000 and 10,000 copies, and can be varied depending on the particular application. As disclosed herein, one particular form of an amplicon is as a nucleic acid "ball" having desired dimensions. The number of copies of the nucleic acid molecule can therefore provide a desired size of a nucleic acid "ball" or a sufficient number of copies for efficient subsequent analysis of the amplicon, for example, sequencing.

The terms "target nucleic acid molecule," "target nucleic acid sequence" or any grammatical equivalent thereof, refers to nucleic acid molecules or sequences that are desired to be detected, sequenced or otherwise analyzed. Any of a variety of desired target nucleic acid sequences can be utilized, including but not limited to exons, or nucleic acid sequences complementary thereto; cDNA sequences, or nucleic acid sequences complementary thereto; untranslated regions (UTRs) or nucleic acids complementary thereto; promoter and/or enhancer regions, or nucleic acid sequences complementary thereto; evolutionary conserved regions (ECRs), or nucleic acid sequences complementary thereto; transcribed genomic regions, or nucleic acid sequences complementary thereto. Any of a variety of methods can be used to obtain targeted nucleic acid sequences, as disclosed herein. Such methods include, but are not limited to, obtaining a targeted nucleic acid molecule using hybridization-extension capture enrichment; using targeted restriction sites, for example, using an oligonucleotide engineered with a hairpin having a Type IIS restriction enzyme site such as a FokI restriction enzyme site and a locus-specific region; using locus-specific hyperbranched rolling circle amplification; using random-locus-specific primer amplification; using multiplex emulsion PCR; using multiplex bridge PCR; using padlock probe amplification; and using mini-libraries from targeted libraries, as disclosed herein.

As used herein, sample nucleic acid sequences refer to nucleic acid sequences obtained from samples that are desired to be analyzed. A nucleic acid sample that is amplified, sequenced or otherwise manipulated in a method disclosed herein can be, for example, DNA or RNA. Exemplary DNA species include, but are not limited to, genomic DNA (gDNA), mitochondrial DNA, chloroplast DNA, episomal DNA, viral DNA and copy DNA (cDNA). One non-limiting example of a subset of genomic DNA is one particular chromosome or one region of a particular chromosome. Exemplary RNA species include, without limitation, coding RNA such as messenger RNA (mRNA), and non-coding RNA (ncRNA) such as transfer RNA (tRNA), microRNA (miRNA), small nuclear RNA (snRNA) and ribosomal RNA (rRNA). Further species of DNA or RNA include fragments or portions of the species listed above or amplified products derived from these species, fragments thereof or portions thereof. The methods described herein are applicable to the above species encompassing all or part of the complement present in a cell. For example, using methods described herein the sequence of a substantially complete genome can be determined or the sequence of a substantially complete targeted nucleic acid sequences such as mRNA or cDNA complement of a cell can be determined.

Useful methods for clonal amplification from single molecules include rolling circle amplification (RCA) (Lizardi et al., *Nat. Genet.* 19:225-232 (1998), which is incorporated herein by reference), bridge PCR (Adams and Kron, *Method for Performing Amplification of Nucleic Acid with Two Primers Bound to a Single Solid Support*, Mosaic Technologies, Inc. (Winter Hill, Mass.); Whitehead Institute for Biomedical Research, Cambridge, Mass., (1997); Adessi et al., *Nucl. Acids Res.* 28:E87 (2000); Pemov et al., *Nucl. Acids Res.* 33:e 11 (2005); or U.S. Pat. No. 5,641,658, each of which is incorporated herein by reference), polony generation (Mitra et al., *Proc. Natl. Acad. Sci. USA* 100:5926-5931 (2003); Mitra et al., *Anal. Biochem.* 320:55-65 (2003), each of which is incorporated herein by reference), and clonal amplification on beads using emulsions (Dressman et al., *Proc. Natl. Acad. Sci. USA* 100:8817-8822 (2003), which is incorporated herein by reference) or ligation to bead-based adapter libraries (Brenner et al., *Nat. Biotechnol.* 18:630-634 (2000); Brenner et al., *Proc. Natl. Acad. Sci. USA* 97:1665-1670 (2000)); Reinartz, et al., *Brief Funct. Genomic Proteomic* 1:95-104 (2002), each of which is incorporated herein by reference). The enhanced signal-to-noise ratio provided by clonal amplification more than outweighs the disadvantages of the cyclic sequencing requirement.

In a particularly useful embodiment, amplicons are generated by rolling circle amplification (RCA), which can be used to generate amplicons having multiple copies of a nucleic acid sequence and which can be used to create nucleic acid "balls," as disclosed herein. It will be understood that these "balls" need not be perfectly spherical and can include other globular or packed conformations. In a particular embodiment, RCA is primed using the at least one universal primer attached to the sample nucleic acid molecule.

As disclosed herein, the amplicons can be compacted prior to hybridizing or binding to a bead described herein. Methods of compacting amplicons are known in the art (for example, as described by Bloomfield, *Curr. Opin. Struct. Biol.* 6(3): 334-41 (1996), and Drmanac et al., US 2007/0099208 A1, each of which is incorporated herein by reference) and disclosed herein. For example, an alcohol or polyamine such as spermine or spermidine can be used. A compacted nucleic acid will have a structure that is more densely packed than the structure of the nucleic acid in the absence of a compacting agent or compacting condition and the structure will typically resemble a ball or globule. The generation of such compacted nucleic acid balls is useful for fabricating one clonal object bound to one bead, as discussed herein in more detail. Various methods can be used to generate balls of a desired size, for example, using various compacting techniques and/or varying the number of copies in an amplicon. Generally, the compacted amplicons have an average diameter or width ranging from about 0.1 µm to about 5 µm, for example, about 0.1 µm, about 0.2 µm, about 0.5 µm, about 1 µm, 2 µm, about 3 µm, about 4 µm and about 5 µm.

Embodiments of the invention provide a method of fabricating an affinity binding patch on a bead by providing a bead having a plurality of first polynucleotides attached to the surface of the bead, wherein the first polynucleotides each have a capture sequence, providing a solid surface having a plurality of second polynucleotides attached to the solid surface, wherein the second polynucleotides each have a capture-complement sequence, a cleavable moiety and an affinity ligand, hybridizing the capture sequences of the first polynucleotides to the capture-complement sequences of the second polynucleotides, thereby forming an immobilized bead on the solid surface, and cleaving the second polynucleotides at the cleavable moiety so as to retain the affinity ligand on the second plurality of polynucleotides, thereby fabricating an affinity binding patch on the bead. In some aspects, the method further includes fabricating one clonal object bound to the affinity binding patch by contacting the affinity ligand with a binding agent, wherein the binding agent has two or more binding sites, and binding one clonal object to the binding agent through a second affinity ligand on the clonal object, wherein the one clonal object has a single tandemly repeated target nucleic acid molecule, thereby fabricating one clonal object bound to the affinity binding patch.

Embodiments of the invention provide a method of fabricating a bead having one clonal object by providing a bead having a plurality of first polynucleotides, providing a solid surface having a plurality of second polynucleotides patterned into patches on the surface, wherein the second polynucleotides each have a cleavable moiety, wherein one clonal object is hybridized to one polynucleotide patch on the surface, and wherein the one clonal object has a single tandemly repeated target nucleic acid molecule, hybridizing the first polynucleotides to the clonal object, thereby forming an immobilized bead on the solid surface, and cleaving the second polynucleotides at the cleavable moiety so as to retain the clonal object, thereby fabricating a bead having one clonal object.

Embodiments of the invention provide a method of fabricating a hybridization patch on a bead by providing a bead having a plurality of first polynucleotides attached to the surface of the bead, wherein the first polynucleotides each have a first capture sequence, providing a solid surface having a plurality of second polynucleotides attached to the solid surface, wherein the second polynucleotides each have a first capture-complement sequence and a second capture-complement sequence, hybridizing the first capture sequences of the first polynucleotides to the first capture-complement sequence of the second polynucleotides, thereby forming an immobilized bead on the solid surface, and extending the first polynucleotides of the immobilized bead using the second capture-complement sequence as a template, thereby fabricating a hybridization patch of extended first polynucleotides on the bead, wherein the extended first polynucleotides have a second capture sequence. The second capture sequence can function as an affinity ligand for attachment of a clonal object. Accordingly, in some aspects, the method further includes fabricating one clonal object bound to the patch on the bead by providing a clonal object having the second capture-complement sequence, or a portion thereof, and hybridizing the second capture-complement sequence, or a portion thereof, of the clonal object to the second capture sequences of the bead, or a portion thereof, thereby fabricating one clonal object bound to the patch on the bead. In some aspects of the method, extending the first polynucleotides includes the addition of one or more nucleoside triphosphate having an affinity ligand, thereby fabricating an affinity binding patch on the bead.

In some aspects, the methods include fabricating one clonal object bound to the affinity binding patch by contacting the affinity ligand with a binding agent, wherein the binding agent has two or more binding sites, and binding one clonal object to the binding agent through a second affinity ligand on the clonal object, wherein the one clonal object has a single tandemly repeated target nucleic acid molecule, thereby fabricating one clonal object bound to the affinity binding patch.

In some aspects, the methods include a step of separating beads that are attached to a clonal object from beads that do not have a clonal object. For example, separation can be carried out based on differences in mass, charge, magnetism or other property imparted by the presence of a clonal object. By way of further example, separation can be carried out based on affinity of a clonal object for a receptor such as a nucleic acid binding protein or an antibody that binds to a ligand on the clonal object. In another example, beads that are bound to a magnetic clonal object can be separated from blank beads using magnetic capture. Separation can be carried out prior to a step of fabricating multiple copies of clonal objects on a solid surface or prior to a step of carrying out a nucleic acid analysis using the clonal objects. In some embodiments, a population of beads having attached clonal objects need not be subjected to a treatment intended to separate out beads lacking clonal objects. In such cases beads can be used directly in a subsequent step of fabricating multiple copies of clonal objects on a solid surface or a step of carrying out a nucleic acid analysis using the clonal objects.

In some aspects of the above embodiments, the methods further include fabricating multiple copies of the clonal object on a second solid surface by providing a second solid surface having a plurality of primer polynucleotides, hybridizing the clonal object to the primer polynucleotides on the second solid surface, and extending the primer polynucleotides to fabricate multiple copies of the clonal object on the second solid surface. The second solid surface can be located on a solid support that is separable from a bead or other surface used in the methods set forth herein. Generally, a first surface and second surface are located on separate or separable solid substrates such as different beads that can be separated from each other, a bead and a well that can be separated from each other, a bead and a planar surface that can be separated from each other, or two planar surfaces that can be separated from each other. However, a first surface region and second surface region can both be located on a single solid support.

In some aspects, the methods described herein include a step of primer extension or "extending" in which a polynucleotide or primer attached to a surface and/or a bead is extended using a complementary polynucleotide hybridized to the primer sequence as a template. The term "extending" or any grammatical equivalent thereof refers to making a first nucleic acid molecule (i.e. primer or polynucleotide) longer by fabricating a copy of a template sequence of a nucleic acid that is hybridized to the first nucleic acid molecule. A single strand can be turned into a double strand by hybridizing a short sequence at one end and extending the short sequence. The extension can be performed using a polymerase and nucleoside triphosphates or a ligase and a set of oligonucleotide cassettes of variable sequences. The extension can be carried out from a universal primer that hybridizes to a sequence common to multiple different nucleic acid templates or an be carried out from a specific primer that hybridizes to a sequence that is unique to a particular template among different templates in a sample.

As used herein, the term "solid surface" is intended to mean the surface of a solid support or substrate and includes any material that can serve as a solid or semi-solid foundation for attachment of polynucleotides, amplicons, DNA balls, other nucleic acids and/or other polymers, including biopolymers. A solid surface of the invention can be modified, for example, to accommodate attachment of nucleic acids by a variety of methods well known to those skilled in the art. Exemplary types of materials comprising solid surfaces include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those exemplified above and multiwell microtier plates. Specific types of exemplary plastics include acrylics, polystyrene, copolymers of styrene and other materials, polypropylene, polyethylene, polybutylene, polyurethanes and Teflon™. Specific types of exemplary silica-based materials include silicon and various forms of modified silicon.

Solid surfaces can also be varied in their shape depending on the application in a method described herein. For example, a solid surface useful in the invention can be planar, or contain regions which are concave or convex. The geometry of the concave or convex regions of the solid surface, in some aspects of the invention, will conform to the size and shape of the bead being attached to the surface. For example, to maximize the contact between as substantially circular bead, the corresponding solid surface may have a diameter that is approximately the same as the substantially circular bead. This can be done to produce a relatively large patch on the surface of the bead since the contact area for transfer between the solid surface and bead is relatively large. Conversely, a relatively small patch can be produced by minimizing the contact area between a bead and a solid surface. For example, a bead having a convex surface can be contacted with a solid surface that is also convex. In this case, the size of the patch will be inversely proportional to the magnitude of curvature for one or both convex surfaces (i.e. the surface area of the patch will decrease as the curvature of the convex surfaces deviate from being flat). Similarly, a bead having a convex surface can be contacted with a flat surface and the size of the patch on the bead will generally be reduced as the curvature of the bead surface increases. In another example, spherical beads can be contacted with a flat surface and the size of the bead can be selected to produce a desired surface area for the patch. In this case, beads having a smaller diameter will generally acquire a smaller patch than beads of a larger diameter.

Figure 8:
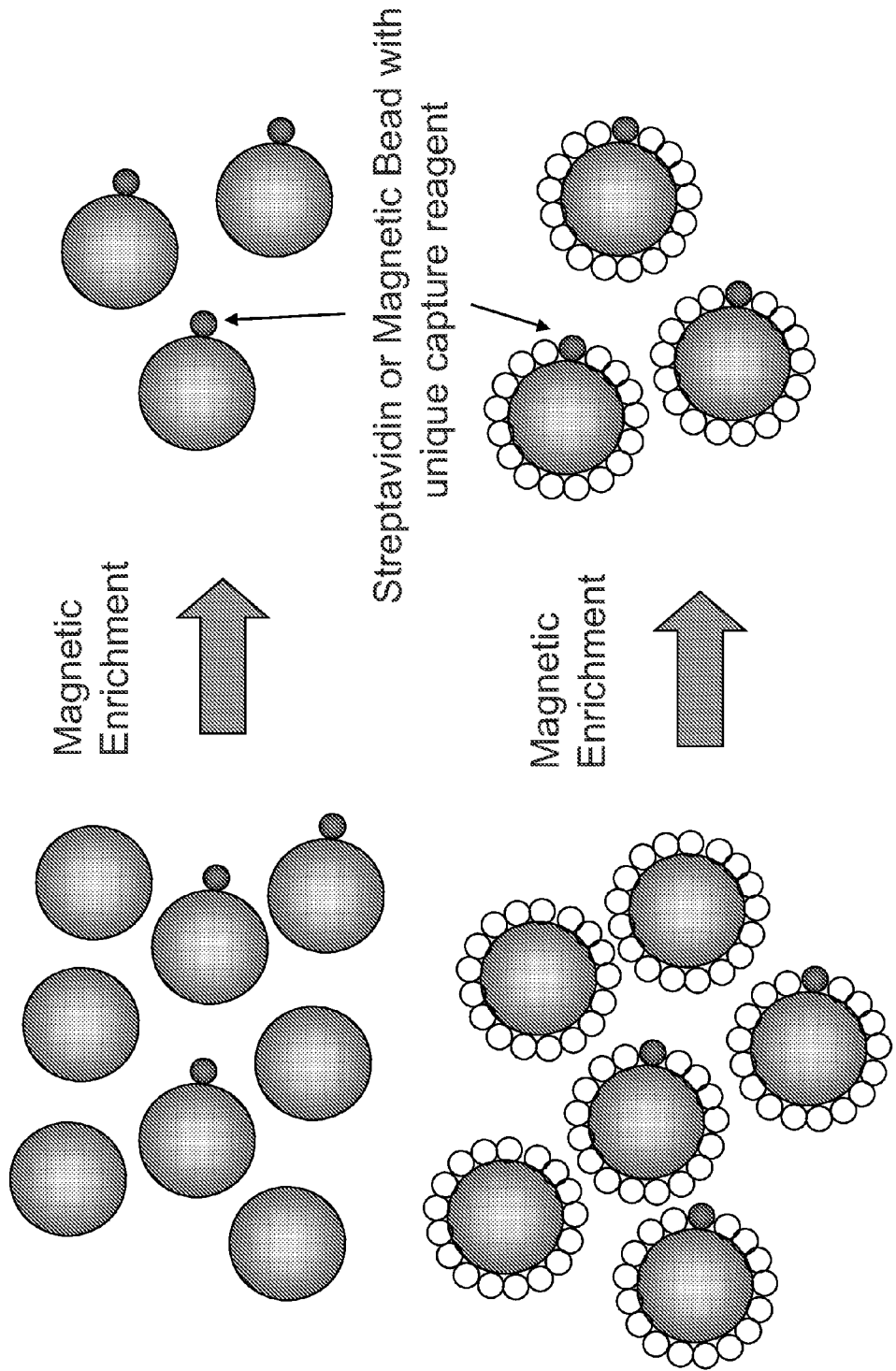
FIG. 8 shows a schematic depiction of magnetically enriching beads contacted with magnetic particles.
Figure 9:
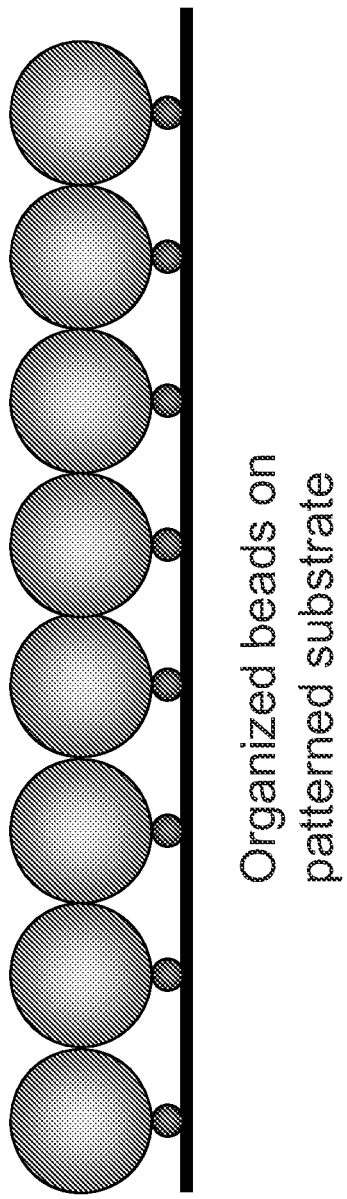
FIG. 9 shows a schematic depiction of beads contacted with particles that are in turn in contact with a patterned surface.

In some embodiments, a solid surface that is used to form an affinity patch on the surface of a bead can be the surface of a smaller particle or bead. For example, a single small particle can be contacted with a larger bead such that a single affinity patch is produced on the surface of the larger bead at the point of contact. A population of beads that each have a single affinity patch can be created in a method wherein an excess of beads are contacted with a scarce amount of particles such that, on average, each bead contacts no more than one particle. If desired, the particles can have a characteristic that allows separation or enrichment of the beads that are bound to particles. For example as shown in FIG. 8, magnetic particles can be used such that particle-bound beads can be separated from blank beads using a magnet. Separation of the particle bound beads can be carried out prior to, during or after creating the affinity patch on the surface of the bead. Another embodiment is shown in FIG. 9, wherein particles are in contact with beads and further arranged on a patterned substrate.

Figure 10:
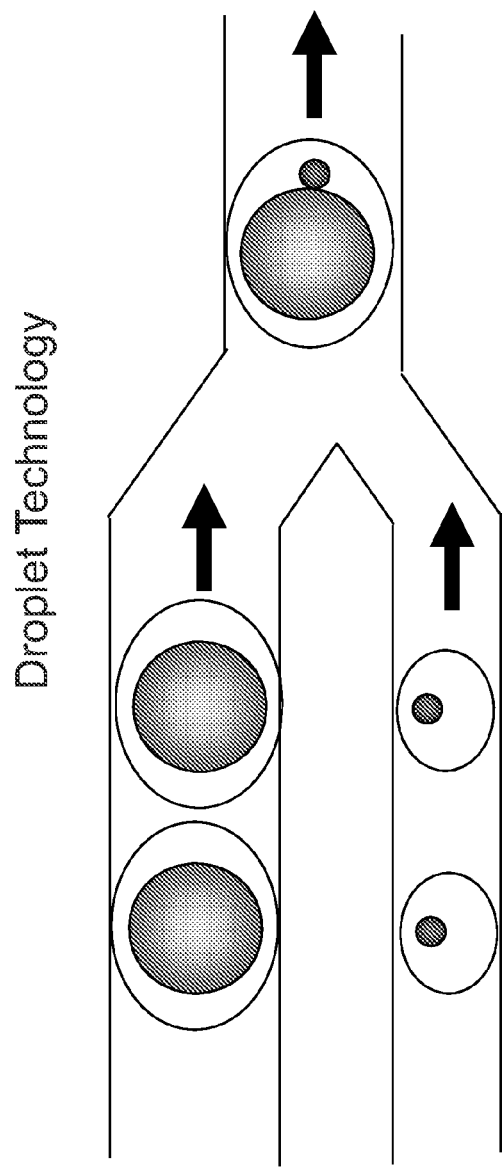
FIG. 10 shows a schematic depiction of mixing bead-bearing droplets with particle bearing droplets to form droplets containing a bead in contact with a single particle.

A population of beads that are to be modified to include an affinity patch can be contacted with particles in solution as exemplified in FIG. 8. Alternatively, beads and particles can be contacted with each other on a larger surface. For example, as shown in Figure FIG. 9, particles can be in contact with a patterned surface and with the larger beads. In this example, the patterned surface can provide a desired spacing between particles to allow each particle to contact a single larger bead. Each of the larger beads can then be modified to include a single affinity patch. In a further embodiment, particles and the beads that will be modified to include an affinity patch can be contacted with each other in an emulsion. An exemplary method for forming emulsion droplets each containing a single bead and single particle is shown in FIG. 10. As shown, droplets containing individual beads can be provided in a first emulsion stream and droplets containing individual particles can be provided in a second fluid stream. The two fluid streams can be mixed in a converging flow device to form an emulsion of droplets containing a single particle in contact with a single bead. If desired, the ratio of particles to beads can be adjusted to provide on average only a single particle in contact with each bead. Also, the particle can include a characteristic that allows separation of bead bearing droplets based on the presence or absence of a particle.

In some aspects of the above methods, the polynucleotides have a universal primer sequence and/or a target nucleic acid molecule. The polynucleotides can be at least 10, 20, 30, 40, 50, 60, 70, 80, 90, 100, 150, 200, 300, 400 or 500 or more nucleotides. Alternatively or additionally, the lengths are no more than 1000, 900, 800, 700, 600, 500, 400, 300, 200, 150, 100, 90, 80, 70, 60, 50, 40, 30 or 20 nucleotides. In some aspects of the above methods, hybridization of the polynucleotides on the bead to the polynucleotides on the solid surface defines the area for the formation of the affinity binding or hybridization patch. This area in some aspects can be less than 1000 $nm^2$, or alternatively less than 500 $nm^2$, or alternatively less than 100 $nm^2$. In some aspect of the above methods, the polynucleotides on the bead when hybridized to the polynucleotides of the solid surface or to a clonal object are further crosslinked together. This crosslinking can occur through the formation of a covalent or ionic bond between the polynucleotides and/or the clonal object.

The term "crosslinking" refers to a process of linking one molecule, such as a polymer chain to another. The bonds linking the molecules can be covalent or ionic bonds. It can be particularly useful to covalently crosslink hybridized sequences so that subsequent steps that may include denaturation of double stranded nucleic acid molecules can be used while still retaining the hybridized polynucleotides. A variety of crosslinking methods can be used so long as the crosslinking does not inhibit subsequent desired reactions with the attached nucleic acid molecules, for example, sequencing. A particularly useful method of crosslinking utilizes psoralen crosslinking. Psoralen can be used to effect crosslinking between pyrimidines on the opposite strands of a hybrid structure.

In some aspects of the methods described herein, a capture moiety, such as a polynucleotide can have a cleavable moiety. Non-limiting examples of cleavable moieties which are useful in the methods include proteins, nucleic acids, polynucleotides, or chemical compounds. In some aspects of the methods, the cleavable moiety is photocleavable. A photocleavable moiety refers to any chemical group that attaches or operably links a polynucleotide to a solid surface as described herein. Photocleavable linkers that can be useful in the methods include, but are not limited to, 2-nitrobenzyl moieties, alpha-substituted 2-nitrobenzyl moieties [e.g. 1-(2-nitrophenyl)ethyl moieties], 3,5-dimethoxybenzyl moieties, thiohydroxamic acid, 7-nitroindoline moieties, 9-phenylxanthyl moieties, benzoin moieties, hydroxyphenacyl moieties, and NHS-ASA moieties. Photocleavable linkers are well known to those skilled in the art (see U.S. Pat. No. 5,739,386, and U.S. Patent Application Publication 2010-0022761, both of which are herein incorporated by reference). In some aspects, the cleavable moiety can be a sequence of nucleotides already present in the polynucleotide itself. For example, the cleavable moiety can be the recognition sequence for an endonuclease, such as a restriction endonuclease, nicking endonuclease or homing endonuclease.

As used herein a "cleavable moiety" refers to a compound which is reactive to a specific catalyst, which upon reacting with the catalyst releases any bound group. Examples of cleavable moieties include compounds that are reactive to, without limitation, proteases, enzymes, chemicals and light. In one aspect of the invention, a cleavable base/bases could be used as the cleavable moiety, such as uracil, which is cleavable by an exogenous base cleaving agent such as DNA glycosylase (UDG) followed by heating or chemical methods which cleave the abasic site. Another example is a restriction enzyme motif cleavable by a restriction enzyme. Similarly, templates having 8-hydroxyguanine can be cleaved by 8-hydroxyguanine DNA glycosylase (FPG protein). Other exemplary exogenous bases and methods for their degradation that can be used are described in U.S. Patent Application Publication 2005-0181394, which is incorporated herein by reference.

Other cleavable moieties are useful for the invention including, a nucleotide having a protease cleavable linker to allow selective cleavage and removal from a solid support. As used herein, the term "protease" is intended to mean an agent that catalyzes the cleavage of peptide bonds in a protein or peptide. Some proteases are non-sequence specific proteases. Generally, for the methods disclosed herein, the protease has sequence specificity, splitting a peptide bond of a protein based on the presence of a particular amino acid sequence in the protein. A protease can be characterized according to the location in a protein where it cleaves, an endoprotease cleaving a protein between internal amino acids of an amino acid chain and an exoprotease cleaving a protein to remove an amino acid from the end of an amino acid chain. In the peptide linkers of the compositions herein, an endoprotease can be used. A protease can be characterized according to its mechanism of action, being identified, for example, as a serine protease, cysteine (thiol) protease, aspartic (acid) protease, metalloprotease or mixed protease depending on the principal amino acid participating in catalysis. A protease can also be classified based on the action pattern, examples of which include an aminopeptidase which cleaves an amino acid from the amino end of a protein, carboxypeptidase which cleaves an amino acid from the carboxyl end of a protein, dipeptidyl peptidase which cleaves two amino acids from an end of a protein, dipeptidase which splits a dipeptide and tripeptidase which cleaves an amino acid from a tripeptide. Typically, a protease is a protein enzyme. However, non-protein agents capable of catalyzing the cleavage of peptide bonds in a protein, especially in a sequence specific manner are also useful in the invention.

The term activity when used in reference to a protease is intended to mean binding of the protease to a protease substrate or hydrolysis of the protease substrate or both. The activity can be indicated, for example, as binding specificity, catalytic activity or a combination thereof. The activity of a protease can be identified qualitatively or quantitatively in accordance with the compositions and methods disclosed herein. Exemplary qualitative measures of protease activity include, without limitation, identification of a substrate cleaved in the presence of the protease, identification of a change in substrate cleavage due to presence of another agent such as an inhibitor or activator, identification of an amino acid sequence that is recognized by the protease, identification of the composition of a substrate recognized by the protease or identification of the composition of a proteolytic product produced by the protease. Activity can be quantitatively expressed as units per milligram of enzyme (specific activity) or as molecules of substrate transformed per minute per molecule of enzyme (molecular activity). The conventional unit of enzyme activity is the International Unit (IU), equal to one micromole of substrate transformed per minute. A proposed coherent Système Internationale (SI) unit is the katal (kat), equal to one mole of substrate transformed per second.

As used herein the term, protease substrate is intended to mean a molecule that can be cleaved by a protease. A protease substrate is typically a protein, protein moiety or peptide having an amino acid sequence that is recognized by a protease. A protease can recognize the amino acid sequence of a protease substrate due to the specific sequence of side chains or due to properties generic to proteins. A protease substrate can also be a protein mimetic or non-protein molecule that is capable of being cleaved or otherwise covalently modified by a protease.

Exemplary proteases, corresponding peptide substrates and their commercial sources are shown in Table 1.

TABLE 1

Proteases and their cleavage preferences.

| Protease | Peptide (cleavage site indicated with dash) | Company |
|---|---|---|
| Thrombin | LVPR-GS | Amersham, Novagen, Sigma, Roche |
| Factor Xa | IEGR-X | Amersham, NEB, Roche |
| Enterokinase | DDDDK-X | NEB, Novagen, Roche |

TABLE 1-continued

Proteases and their cleavage preferences.

| Protease | Peptide (cleavage site indicated with dash) | Company |
|---|---|---|
| TEV protease | ENLYFQ-G | Invitrogen |
| PreScission | LEVLFQ-GP | Amersham |
| HRV 3C Protease | LEVLFQ-GP | Novagen |
| Trypsin | R-X, K-X | |
| Endoproteinase Asp-N | X-D | |
| Chymotrypsin | Y-X, F-X, W-X | |
| Endoproteinase Glu-C | E-X | |
| Endoproteinase Arg-C | R-X | |
| Endoproteinase Lys-C | K-X | |

Protease cleavable linkers used in the invention are generally peptides. Peptide synthesis can be carried out using standard solid phase or solution phase chemistry, as desired. Methods for peptide synthesis are well known to those skilled in the art (Fodor et. al., *Science* 251:767 (1991); Gallop et al., *J. Med. Chem.* 37:1233-1251 (1994); Gordon et al., *J. Med. Chem.* 37:1385-1401 (1994)). It is understood that a peptide linker can be synthesized and then added to the NTP as a peptide or can be synthesized by sequentially adding amino acids and then a dye.

Embodiments of the invention provide a method of amplifying a target nucleic acid molecule by placing the compositions or populations of beads having affinity bound or hybridized clonal objects described herein onto a solid surface having microwells, wherein only one bead can spatially fit into one microwell and amplifying the target nucleic acid molecules in the microwells, thereby forming amplicons. In some aspects of the invention, the method further includes determining the nucleic acid sequence of the target nucleic acid molecule. In one aspect, determining the nucleic acid sequence of the target nucleic acid molecule includes sequencing the amplified target nucleic acid molecules, thereby determining the nucleic acid sequence of the target nucleic acid molecule.

In some aspects, determining the nucleic acid sequence of the target nucleotide molecule further includes quantifying the target nucleic acid molecule or amplicons. Methods for quantifying a target nucleic acid molecule or amplicon are well known to one of skilled in the art. For example, during amplification of the target nucleic acid, quantitative techniques such as real-time polymerase chain reaction (RT-PCR) can be used to quantify the copy number of target nucleic acid molecules present in the clonal object as discussed in Logan et al. *Real-Time PCR: Current Technology and Applications*, Caister Academic Press. (2009). Briefly, RT-PCR follows the general principle of polymerase chain reaction, however inclusion of detection molecules, such as non-specific fluorescent dyes that intercalate with any double-stranded DNA, or sequence-specific DNA probes consisting of oligonucleotides that are labeled with a fluorescent reporter, which permits detection only after hybridization of the probe with its complementary DNA target, allows for the detection of nucleic acid formed during amplification. The rate of detectable molecules is proportional to the copy number of target nucleic acid molecules present in the clonal object. Furthermore, quantifying the target nucleic acid molecule or amplicons can be done following amplification using standard gel electrophoresis and/or Southern blot techniques, which are well practiced in the art.

In some aspects, the method includes hybridizing a probe nucleic acid to the amplicon, thereby identifying the target nucleic acid molecule. Methods of hybridizing a probe nucleic acid to identify the target nucleic acid molecule are well know to one skilled in the art and examples of such methods are described here. For example, an oligonucleotide ligation assay (OLA), as described below, is a method that utilizes hybridizing a probe to identify the target nucleic acid molecule.

In some aspects of the method, the solid surface is a microarray, which can have microwells having a diameter sufficient to allow only one bead having the clonal object into the well. It is understood that the size of the microwell will be dependent upon the size of the bead and/or the size of the clonal object. In some aspects of the invention, the diameter of the microwells are less than 200 μm, or alternatively less than 100 μm, or alternatively less than 50 μm, or alternatively less than 40 μm, or alternatively less than 30 μm, or alternatively less than 20 μm, or alternatively less than 10 μm, or alternatively less than 5 μm. It is also understood that the size of the microwells on the microarray can be of various sizes and will ultimately depend on the systems and/or apparatus used to analyze later reactions.

In some aspects, the method includes amplifying the clonal object or in some aspects the target nucleic acid molecules present in the clonal object. Methods of amplifying nucleic acid sequences are well know to one of skill in the art. Particularly useful methods for amplifying the target nucleic acids includes, but is not limited to, solid-phase clonal amplification. Solid-phase clonal amplification can be done using a number of PCR techniques known in the art such as bridge amplification using two or more primer polynucleotides immobilized on a bead or solid surface. Useful bridge amplification methods include those where one or both of the primers used for amplification are attached to a solid phase as described, for example, in US 2008/0286795; US 2007/0128624 and US 2008/0009420, each of which is incorporated herein by reference. Another useful method for solid-phase clonal amplification is multiple displacement amplification.

In some aspects, the methods for amplifying a target nucleic acid molecule further includes cleaving between the tandem repeats of the single tandemly repeated target nucleic acid molecule, i.e. DNA ball or circular library element, prior to amplifying the target nucleic acid molecules. This cleaving step generates a population of target nucleic acid molecules, which can be more readily accessible to later amplification reactions, such as PCR or bridge amplification methods. In some aspects of the method, the cleavage step includes hybridizing an oligonucleotide to the clonal object and cleaving the clonal object by an enzyme, such as, but not limited to, a homing endonuclease, a restriction endonuclease or a nicking endonuclease. These endonucleases are well known to those skilled in the art and are available from several sources (New England Biolabs—Ipswich, Mass.; Promega Corporation—Madison, Wis. and Life Technologies—Carlsbad, Calif.).

The expression "amplification" or "amplifying" includes methods such as PCR, ligation amplification (or ligase chain reaction, LCR), multiple displacement amplification (MDA) and other amplification methods. These methods are known and widely practiced in the art. See, e.g., U.S. Pat. Nos. 4,683,195 and 4,683,202 and Innis et al., "PCR protocols: a guide to method and applications" Academic Press, Incorporated (1990) (for PCR); and Wu et al. (1989) *Genomics* 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Amplification methods set forth herein can be carried out on the surface of a bead or on the surface of an array substrate following transfer of the bead to the array. For example, a bead having a clonal object can be transferred to a well in an array of wells and the clonal object can be amplified in the well. The amplification method can include those where one or both of the primers used for amplification are attached to the bead or to the surface of the array, for example, the inner surface of a well. In particular embodiments, MDA primers can be attached to the surface of a bead, well or other surface such that the MDA primers come into contact with a clonal object and the clonal object is amplified. The resulting amplicons can be concatameric copies of the clonal object that are attached to the bead, well or other surface. Amplification need not be carried out using solid phase primer(s) and can instead be carried out in solution such that different target sequences are separated from each other by isolation in a well, emulsion droplet or other reaction vessel. In some embodiments amplification can include both the use of solid phase amplification primer (s) as well as isolation of target nucleic acids in a well, emulsion droplet or other reaction vessel.

Reagents and hardware for conducting amplification reaction are commercially available. Primers useful to amplify sequences from a particular gene region are preferably complementary to, and hybridize specifically to sequences in the target region or in its flanking regions and can be prepared using the polynucleotide sequences provided herein. Nucleic acid sequences generated by amplification may be sequenced directly. Alternatively the amplified sequence(s) may be cloned prior to sequence analysis. Methods for the direct cloning and sequence analysis of enzymatically amplified genomic segments are known in the art.

One method to eliminate primer-dimer interactions, which are often associated with traditional PCR, is to perform solid-phase PCR using primer pairs physically separated on beads as a multiplex bridge PCR reaction (Adams et al., U.S. Pat. No. 5,641,658). Each primer set can be individually co-immobilized and then later all the beads are mixed together to form one grand master mix. This master bead mix can be inoculated into the PCR mix along with all the other PCR components and target DNA. Key parameters in the solid-phase amplification reaction can be varied including, but not limited to, linker length between the primer and beads. After amplification, the library elements can be cleaved from the beads and processed as a standard library for generation of clonal arrays.

In some aspects, the method for determining the nucleic acid sequence of a target nucleic acid molecule includes sequencing, which is well known to one skilled in the art. In some aspects, sequencing by synthesis, sequencing by ligation or sequencing by hybridization is used for deterring the nucleic acid sequence of a target nucleic acid molecule. Nucleic acid sequencing has become an important technology with widespread applications, including mutation detection, whole genome sequencing, exon sequencing, mRNA or cDNA sequencing, alternate transcript profiling, rare variant detection, and clone counting, including digital gene expression (transcript counting) and rare variant detection. As disclosed herein, various amplification methods can be employed to generate larger quantities, particularly of limited nucleic acid samples, prior to sequencing. For example, the amplification methods can produce a targeted library of amplicons. The amplicons whether or not they are targeted amplicons can be in the form of DNA balls.

Two useful approaches for high throughput or rapid sequencing are sequencing by synthesis (SBS) and sequencing by ligation. Target nucleic acid of interest can be amplified, for example, using ePCR, as used by 454 Lifesciences (Branford, Conn.) and Roche Diagnostics (Basel, Switzerland). Nucleic acid such as genomic DNA or others of interest can be fragmented, dispersed in water/oil emulsions and diluted such that a single nucleic acid fragment is separated from others in an emulsion droplet. A bead, for example, containing multiple copies of a primer, can be used and amplification carried out such that each emulsion droplet serves as a reaction vessel for amplifying multiple copies of a single nucleic acid fragment. Other methods can be used, such as bridging PCR (Illumina, Inc.; San Diego Calif.), or polony amplification (Agencourt/Applied Biosystems).

For sequencing by ligation, labeled nucleic acid fragments are hybridized and identified to determine the sequence of a target nucleic acid molecule. For sequencing by synthesis (SBS), labeled nucleotides can be used to determine the sequence of a target nucleic acid molecule. A target nucleic acid molecule can be hybridized with a primer and incubated in the presence of a polymerase and a labeled nucleotide containing a blocking group. The primer is extended such that the nucleotide is incorporated. The presence of the blocking group permits only one round of incorporation, that is, the incorporation of a single nucleotide. The presence of the label permits identification of the incorporated nucleotide. Either single bases can be added or, alternatively, all four bases can be added simultaneously, particularly when each base is associated with a distinguishable label. After identifying the incorporated nucleotide by its corresponding label, both the label and the blocking group can be removed, thereby allowing a subsequent round of incorporation and identification. Thus, it is desirable to have conveniently cleavable linkers linking the label to the base, such as those disclosed herein, in particular peptide linkers. Additionally, it is advantageous to use a removable blocking group so that multiple rounds of identification can be performed, thereby permitting identification of at least a portion of the target nucleic acid sequence. The compositions and methods disclosed herein are particularly useful for such an SBS approach. In addition, the compositions and methods can be particularly useful for sequencing from an array, where multiple sequences can be "read" simultaneously from multiple positions on the array since each nucleotide at each position can be identified based on its identifiable label. Exemplary methods are described in US 2009/0088327; US 2010/0028885; and US 2009/0325172, each of which is incorporated herein by reference.

The oligonucleotides, nucleosides and nucleotides described herein can be particularly useful for nucleotide sequence characterization or sequence analysis. Reversible labeling, reversible termination or a combination thereof can allow accurate sequencing analysis to be efficiently performed. Methods for manual or automated sequencing are well known in the art and include, but are not limited to, Sanger sequencing, Pyrosequencing, sequencing by hybridization, sequencing by ligation and the like. Sequencing methods can be preformed manually or using automated methods. Furthermore, the amplification methods set forth herein can be used to prepare nucleic acids for sequencing using commercially available methods such as automated Sanger sequencing (available from Applied Biosystems, Foster City, Calif.) or Pyrosequencing (available from 454 Lifesciences, Branford, Conn. and Roche Diagnostics, Basel, Switzerland); for sequencing by synthesis methods commercially available from Illumina, Inc. (San Diego, Calif.) or Helicos (Cambridge, Mass.) or sequencing by ligation methods being developed by Applied Biosystems in its Agencourt platform (see also Ronaghi et al., *Science* 281:363 (1998); Dressman et al., *Proc. Natl. Acad. Sci. USA* 100:8817-8822 (2003); Mitra et al., *Proc. Natl. Acad. Sci. USA* 100:55926-5931 (2003)).

A population of nucleic acids, such as DNA balls or other amplicons set forth herein, can be sequenced using methods in which a primer is hybridized to each nucleic acid such that the nucleic acids form templates and modification of the primer occurs in a template directed fashion. The modification can be detected to determine the sequence of the template. For example, the primers can be modified by extension using a polymerase and extension of the primers can be monitored under conditions that allow the identity and location of particular nucleotides to be determined. For example, extension can be monitored and sequence of the template nucleic acids determined using Pyrosequencing which is described in U.S. Patent Application Publications 2005/0130173 and 2006/0134633 and U.S. Pat. Nos. 4,971,903; 6,258,568 and 6,210,891, each of which is incorporated herein by reference, and is also commercially available. Extension can also be monitored according to addition of labeled nucleotide analogs by a polymerase, using methods described, for example, in U.S. Pat. No. 4,863,849; U.S. Pat. No. 5,302,509; U.S. Pat. No. 5,763,594; U.S. Pat. No. 5,798,210; U.S. Pat. No. 6,001,566; U.S. Pat. No. 6,664,079; U.S. 2005/0037398; and U.S. Pat. No. 7,057,026, each of which is incorporated herein by reference. Polymerases useful in sequencing methods are typically polymerase enzymes derived from natural sources. It will be understood that polymerases can be modified to alter their specificity for modified nucleotides as described, for example, in WO 01/23411; U.S. Pat. No. 5,939,292; and WO 05/024010, each of which is incorporated herein by reference. Furthermore, polymerases need not be derived from biological systems. Polymerases that are useful in the invention include any agent capable of catalyzing extension of a nucleic acid primer in a manner directed by the sequence of a template to which the primer is hybridized. Typically polymerases will be protein enzymes isolated from biological systems.

A further modification of primers that can be used to determine the sequence of templates to which they are hybridized is ligation. Such methods are referred to as sequencing by ligation and are described, for example, in Shendure et al. *Science* 309:1728-1732 (2005); U.S. Pat. No. 5,599,675; and U.S. Pat. No. 5,750,341, each of which is incorporated herein by reference. It will be understood that primers need not be modified in order to determine the sequence of the template to which they are attached. For example, sequences of template nucleic acids can be determined using methods of sequencing by hybridization such as those described in U.S. Pat. No. 6,090,549; U.S. Pat. No. 6,401,267 and U.S. Pat. No. 6,620,584. It is understood that many of the uses of compositions of the present invention can be applied to both sequencing by synthesis (SBS) or single base extension (SBE), since both utilize extension reactions.

A DNA ball or other amplicons produced using methods set forth herein can be used in an extension assay. Extension assays are useful for detection of alleles, mutations or other nucleic acid features in an amplicon of interest. Extension assays are generally carried out by modifying the 3' end of a first nucleic acid when hybridized to a second nucleic acid such as a DNA ball or other amplicon. The amplicon can act as a template directing the type of modification, for example, by base pairing interactions that occur during polymerase-based extension of the first nucleic acid to incorporate one or more nucleotide. Polymerase extension assays are particularly useful, for example, due to the relative high-fidelity of polymerases and their relative ease of implementation. Extension assays can be carried out to modify nucleic acid probes that have free 3' ends, for example, when bound to a substrate such as an array. Exemplary approaches that can be used include, for example, allele-specific primer extension (ASPE), single base extension (SBE), degenerate probe ligation such as that used in the SOLiD system sold by Life Technologies (Carlsbad, Calif.) or Pyrosequencing as described, for example, in U.S. 2005/0181394, which is incorporated herein by reference. A nucleic acid, nucleotide or nucleoside having a reversible blocking group on a 2', 3' or 4' hydroxyl, a peptide linked label or a combination thereof can be used in such methods. For example the nucleic acid, nucleotide or nucleoside can be included in the first nucleic acid or the second nucleic acid. Additionally or alternatively, the nucleic acid, nucleotide or nucleoside can be used to modify the free 3' ends in the extension reactions.

In particular embodiments, single base extension (SBE) can be used for detection of an allele, mutations or other nucleic acid features. The compositions of the present invention are useful in an SBE method, in particular, a nucleoside or nucleotide containing a peptide linker, allowing cleavage and removal of a label, and/or terminator blocking group, either removable or non-removable. Briefly, SBE utilizes an extension probe that hybridizes to a target genome fragment at a location that is proximal or adjacent to a detection position, the detection position being indicative of a particular locus. A polymerase can be used to extend the 3' end of the probe with a nucleotide analog labeled with a detection label such as those described previously herein. Based on the fidelity of the enzyme, a nucleotide is only incorporated into the extension probe if it is complementary to the detection position in the target nucleic acid. If desired, the nucleotide can be derivatized such that no further extensions can occur using a blocking group, including reversible blocking groups, and thus only a single nucleotide is added. The presence of the labeled nucleotide in the extended probe can be detected for example, at a particular location in an array and the added nucleotide identified to determine the identity of the locus or allele. SBE can be carried out under known conditions such as those described in U.S. patent application Ser. No. 09/425,633. A labeled nucleotide can be detected using methods known to one of skill in the art, such as those described in Syvanen et al., *Genomics* 8:684-692 (1990); Syvanen et al., *Human Mutation* 3:172-179 (1994); U.S. Pat. Nos. 5,846,710 and 5,888,819; and Pastinen et al., *Genomics Res.* 7(6):606-614 (1997).

ASPE is an extension assay that utilizes extension probes that differ in nucleotide composition at their 3' end. An ASPE method can be performed using a nucleoside or nucleotide containing a cleavable linker, so that a label can be removed after a probe is detected. This allows further use of the probes or verification that the signal detected was due to the label that has now been removed. Briefly, ASPE can be carried out by hybridizing a sample nucleic acid, or amplicons derived therefrom, to an extension probe having a 3' sequence portion that is complementary to a detection position and a 5' portion that is complementary to a sequence that is adjacent to the detection position. Template directed modification of the 3' portion of the probe, for example, by addition of a labeled nucleotide by a polymerase yields a labeled extension product, but only if the template includes the target sequence. The presence of such a labeled primer-extension product can then be detected, for example, based on its location in an array to indicate the presence of a particular allele.

In particular embodiments, ASPE can be carried out with multiple extension probes that have similar 5' ends such that they anneal adjacent to the same detection position in a target nucleic acid but different 3' ends, such that only probes having a 3' end that complements the detection position are modified by a polymerase. A probe having a 3' terminal base that is complementary to a particular detection position is referred to as a perfect match (PM) probe for the position, whereas probes that have a 3' terminal mismatch base and are not capable of being extended in an ASPE reaction are mismatch (MM) probes for the position. The presence of the labeled nucleotide in the PM probe can be detected and the 3' sequence of the probe determined to identify a particular allele at the detection position.

A sequence or allele present in an amplicon, such as a DNA ball, can be detected using a ligation assay such as oligonucleotide ligation assay (OLA). Detection with OLA involves the template-dependent ligation of two smaller probes into a single long probe, using a target sequence in an amplicon as the template. In a particular embodiment, a single-stranded target sequence includes a first target domain and a second target domain, which are adjacent and contiguous. A first OLA probe and a second OLA probe can be hybridized to complementary sequences of the respective target domains. The two OLA probes are then covalently attached to each other to form a modified probe. In embodiments where the probes hybridize directly adjacent to each other, covalent linkage can occur via a ligase. One or both probes can include a nucleoside having a label such as a peptide linked label. Accordingly, the presence of the ligated product can be determined by detecting the label. In particular embodiments, the ligation probes can include priming sites configured to allow amplification of the ligated probe product using primers that hybridize to the priming sites, for example, in a PCR reaction.

Alternatively, the ligation probes can be used in an extension-ligation assay wherein hybridized probes are non-contiguous and one or more nucleotides are added along with one or more agents that join the probes via the added nucleotides. Furthermore, a ligation assay or extension-ligation assay can be carried out with a single padlock probe instead of two separate ligation probes. The ends of the padlock probe are designed to complement adjacent or proximal sequence regions in an amplicon or other template such that ligation or extension followed by ligation results in a circularized padlock probe. The probe can be amplified by rolling circle amplification. Exemplary conditions for ligation assays or extension-ligation assays using separate probes or ligation probes are described, for example, in U.S. Pat. No. 6,355,431 B1 and U.S. 2003/0211489, each of which is incorporated herein by reference.

A ligation probe such as a padlock probe used in the invention can further include other features such as an adaptor sequence, restriction site for cleaving concatemers, a label sequence or a priming site for priming an amplification reaction as described, for example, in U.S. Pat. No. 6,355,431 B1.

It is understood that modifications which do not substantially affect the activity of the various embodiments of this invention are also provided within the definition of the invention provided herein. Accordingly, the following examples are intended to illustrate but not limit the present invention.

Example I

Loading Microbeads with Single Stranded Targets for DNA Sequencing

Certain types of DNA sequencing techniques, such as Pyrosequencing, when utilized in a high throughput multi-well system require that sufficient single stranded target DNA is present in each microwell in order to produce a robust signal and in the case of Pyrosequencing for every cycle of dNTP addition. Furthermore, each microwell must typically contain only a single DNA target sequence with several copies of the target sequence in order to have a clear signal above any detectable background. The following method described herein achieves both of these requirements for a system designed to perform both PCR and sequencing on the same platform.

Briefly, the following method is based on rolling circle amplification (RCA) to produce DNA balls from discreet DNA sequences. DNA balls are then bound to primer loaded microbeads that contain a binding spot of a sufficient size that excludes the binding of more than one DNA ball per microbead. After the DNA balls have been attached to the microbeads, the microbeads are placed into the microwells of a PCR/sequencing platform. The multiple copies of the tandemly repeated target sequences are then cut to produce numerous single stranded DNA target sequences. These identical target sequences have primer sequences (P1'), which are complementary to the primers (P1) attached to the microbead, and the primer sequence (P2). P1' sequences are annealed to P1 primers on the bead and PCR is performed with P2 primers in solution. After amplification by PCR, all DNA fragments, which are not covalently attached to the beads are removed. After this step, the beads are ready for sequencing.

Production of Microbeads with Affinity Binding Patch

Polynucleotide primers having a P1 sequence are attached to microbeads using methods described in U.S. Pat. No. 7,259,258 (incorporated herein by reference) thereby generating a pool of charged microbeads (FIG. 1). The preferred size of the microbeads for generating the desired affinity binding patch is 10-15 μm for attaching an RCA product having 100-1000 copies of the target sequence (~200-500 nm patch diameter). However, the size of the beads can be varied depending on the length of the primers attached to the bead and the size of the DNA ball to be attached. A plate charged with biotinylated primers having a complementary P1' sequence are generated using microfabrication lithography (FIG. 1). The biotinylated primers are attached to the plate through a linker which has a cleavable moiety, such as a photocleavable linking group. Next the charged microbeads are hybridized to the surface of the plate.

Figure 2:
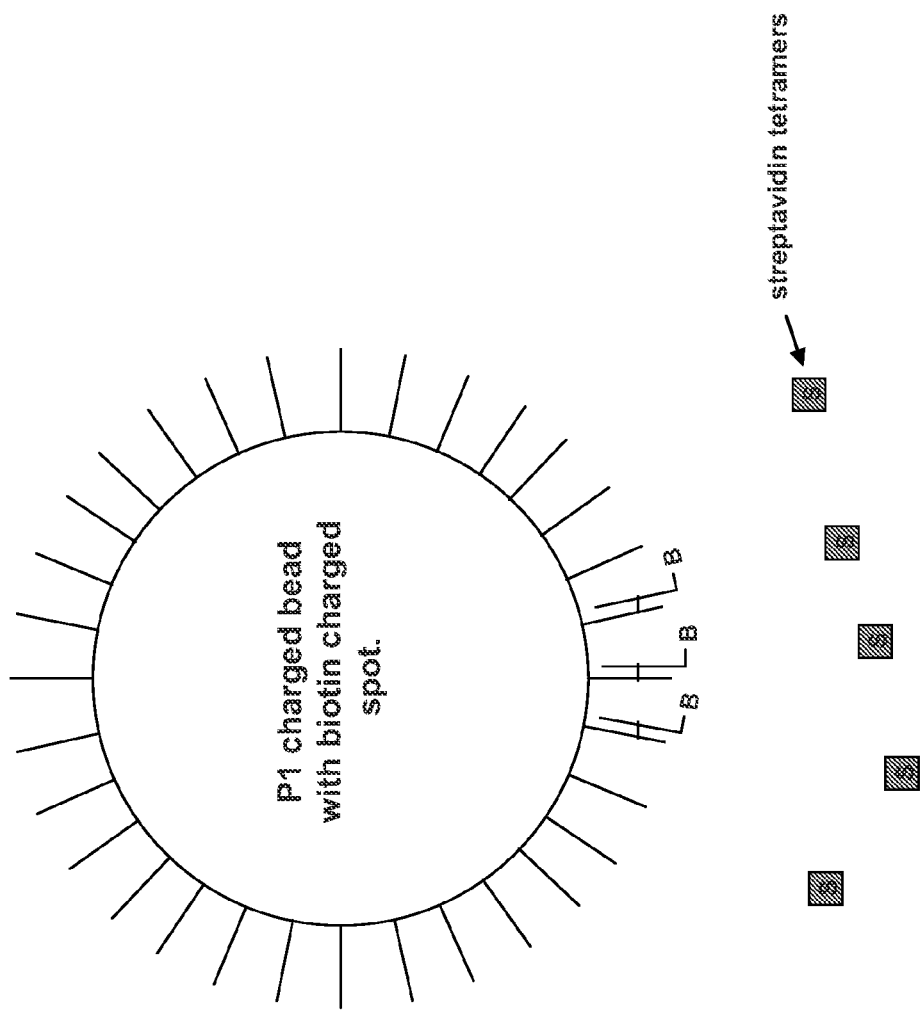
FIG. 2 shows a schematic depiction of a bead charged with (P1) primer polynucleotides shown in FIG. 1 after hybridization to the complementary biotinylated (P1') primer polynucleotide, crosslinking of the P1 primer to the P1' primer and cleaving of the linker having a cleavable moiety thereby retaining the affinity ligand biotin on the P1' primer. Also depicted is contacting the bead with the binding agent streptavidin tetramers. (B) represent the affinity ligand biotin. Square shaded boxes including the designation (S) represent the streptavidin tetramers.

Once the charged beads have been immobilized to the surface of the plate, the hybridized primers can be optionally crosslinked to form a more stable bond between the two primers. Crosslinking of the primers is done through introduction of psoralen. Psoralen can be introduced to a primer by incorporating a psoralen labeled T phosphoramidite during standard phosphodiester oligonucleotide synthesis chemistry. Next the immobilized beads are released from the plate by cleaving the linker with light of an appropriate wavelength to cleave the photochemical linker. The unbound P1' primers are separated from the released microbeads, generating a P1 charged microbead with a biotin charged spot located at one region of the bead (FIG. 2).

Figure 3:
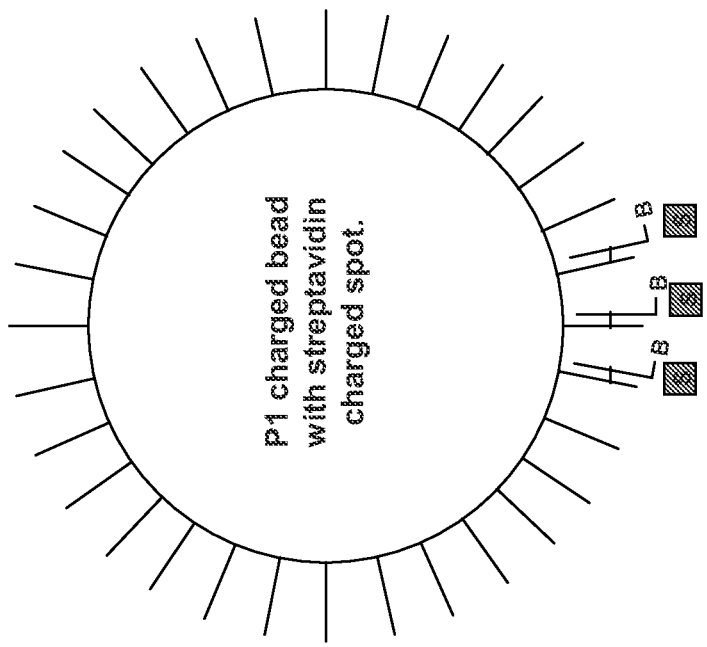
FIG. 3 shows schematic depictions of side and face views of a bead having an affinity binding patch charged with streptavidin tetramers.
Figure 3:
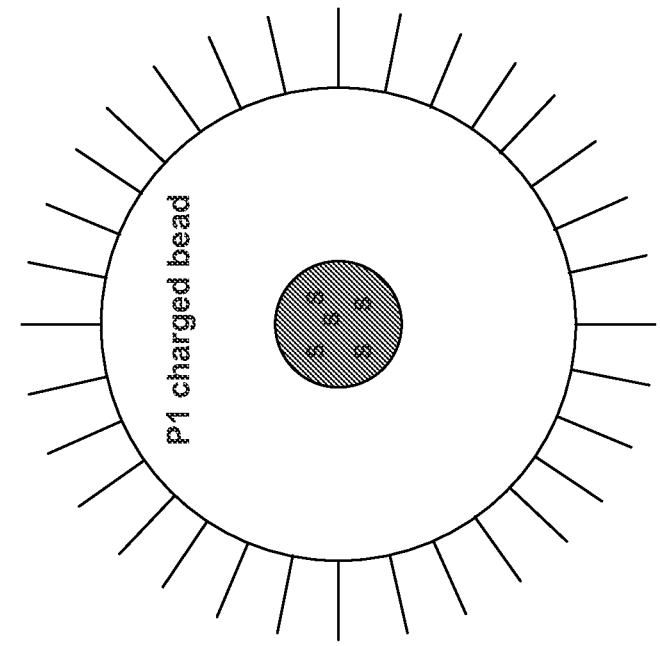

The beads generated above are then challenged with streptavidin tetramers. The streptavidin tetramers are capable of binding more than one biotin and thus after the spot is charged with streptavidin, the beads are now capable of binding to another biotin molecule (FIG. 3). The beads now contain an affinity binding patch of streptavidin tetramers capable of binding a biotinylated DNA ball.

Generation of DNA Balls

Figure 4:
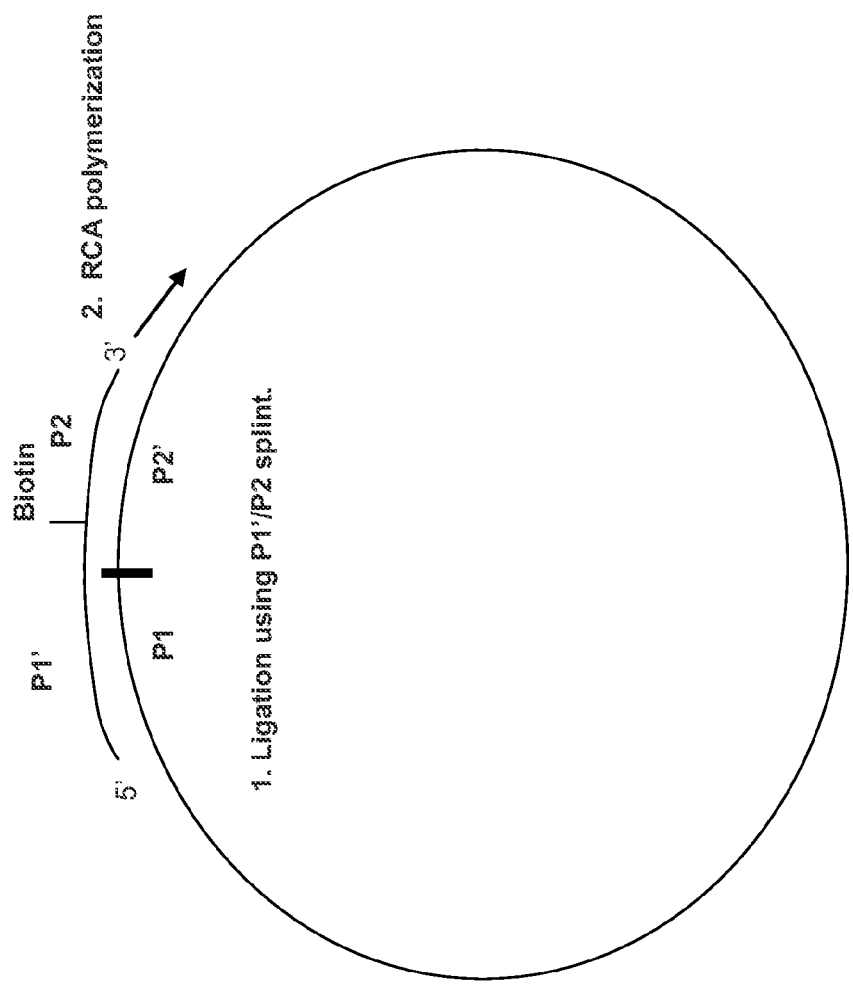
FIG. 4 shows a schematic depiction of single stranded target fragment ligated into a single stranded nucleic acid molecule where the ligation splint having P1' and P2 sequences complementary to the single stranded P1 and P2' sequences serves as the primer for rolling circle amplification (RCA). The primer having a complementary P1' and P2 sequence can optionally be biotinylated (B).
Figure 5:
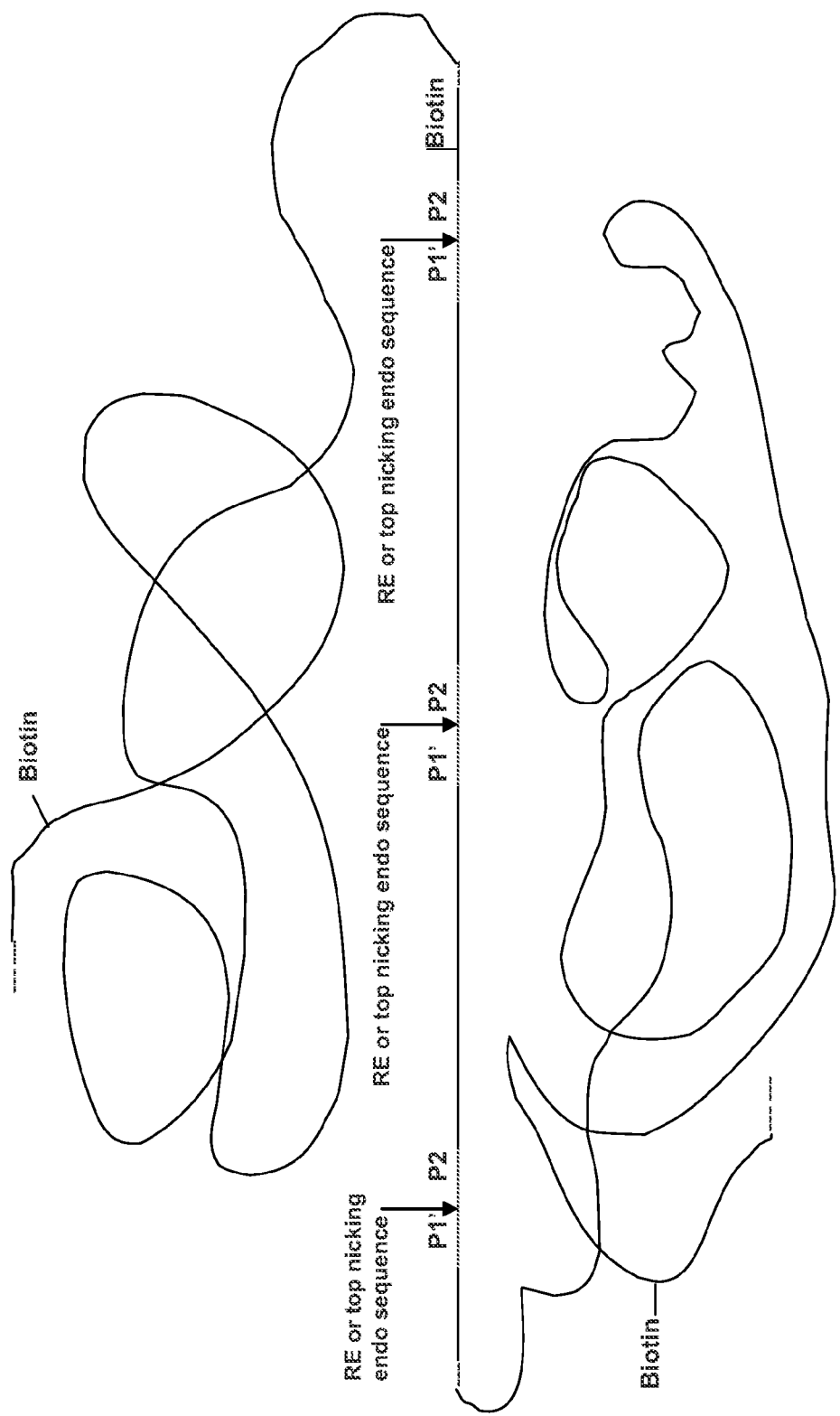
FIG. 5 shows a schematic depiction of a DNA ball having tandemly repeated target nucleic acid molecules separated by primer sequences P1' and P2. The primer sequences also include restriction endonuclease (RE) or top nicking endonuclease recognition sequences. The DNA ball can optionally be biotinylated at either end of the DNA molecule or within the DNA ball by incorporation of a biotinylated nucleotide during amplification.

Target DNA molecules are generated by adapter ligation approaches such as those described in US 2007/0128624 and US 2008/0009420 (each of which is incorporated herein by reference) to have P1 and P2' primer sequence attached to the 5' and 3' ends of the DNA molecule, respectively. The target DNA molecules are then denatured by heat and/or 0.1 N NaOH to generate single stranded molecules. The single stranded target molecules are hybridized to splint primer polynucleotides having the complementary primer sequences P1' and P2 (FIG. 4). The splint primer polynucleotides can also contain one or more biotinylated nucleotide for later binding to the microbeads. Additionally, the P1' and P2 sequences can be constructed to contain a restriction enzyme or top nicking endonuclease recognition sequence for later cleavage (FIG. 5). Using the splint to generate a double stranded DNA molecule, the complementary ends of the single stranded target molecules are ligated to each other by T4 DNA ligase forming a single stranded DNA template (FIG. 4).

After ligation, the splint is used as the primer in rolling circle amplification (RCA) to produce a DNA ball. RCA is conducted by extending the splint primer using phi29 polymerase and nucleotides. A low percentage of biotinylated dNTPs can be included in this amplification reaction in order to label 10% or fewer of the tandem sequences in the DNA ball. Incorporation of the these additional biotinylated dNTPs will facilitate efficient binding to the affinity binding patch of the microbead by increasing the likelihood that a biotin molecule is exposed to the outer surface of the DNA ball.

Amplification and Sequencing of Target DNA

Microbeads containing an affinity binding spot as described above are attached to the DNA balls by binding of the biotin on the splint primer (which was incorporated into the DNA ball during RCA) to the streptavidin molecules at the patch. More specifically, the streptavidin acts as an intermediary to bind the DNA ball to the beads because the streptavidin molecules that are bound to the patches (as shown in FIG. 3) are tetrameric and can therefore bind to the biotin on the P1 charged bead and to the biotin on the DNA ball.

After the DNA balls have been attached to the microbeads (one per microbead), the microbeads are placed into the microwells of the PCR/sequencing platform by random deposition as described for example in U.S. Pat. No. 7,622,294, which is incorporated herein by reference. The size and shape of the microwells is such that only one microbead can fit into a microwell. The microwells are also separated from each other so that PCR and sequencing can be done in each well.

Figure 6:
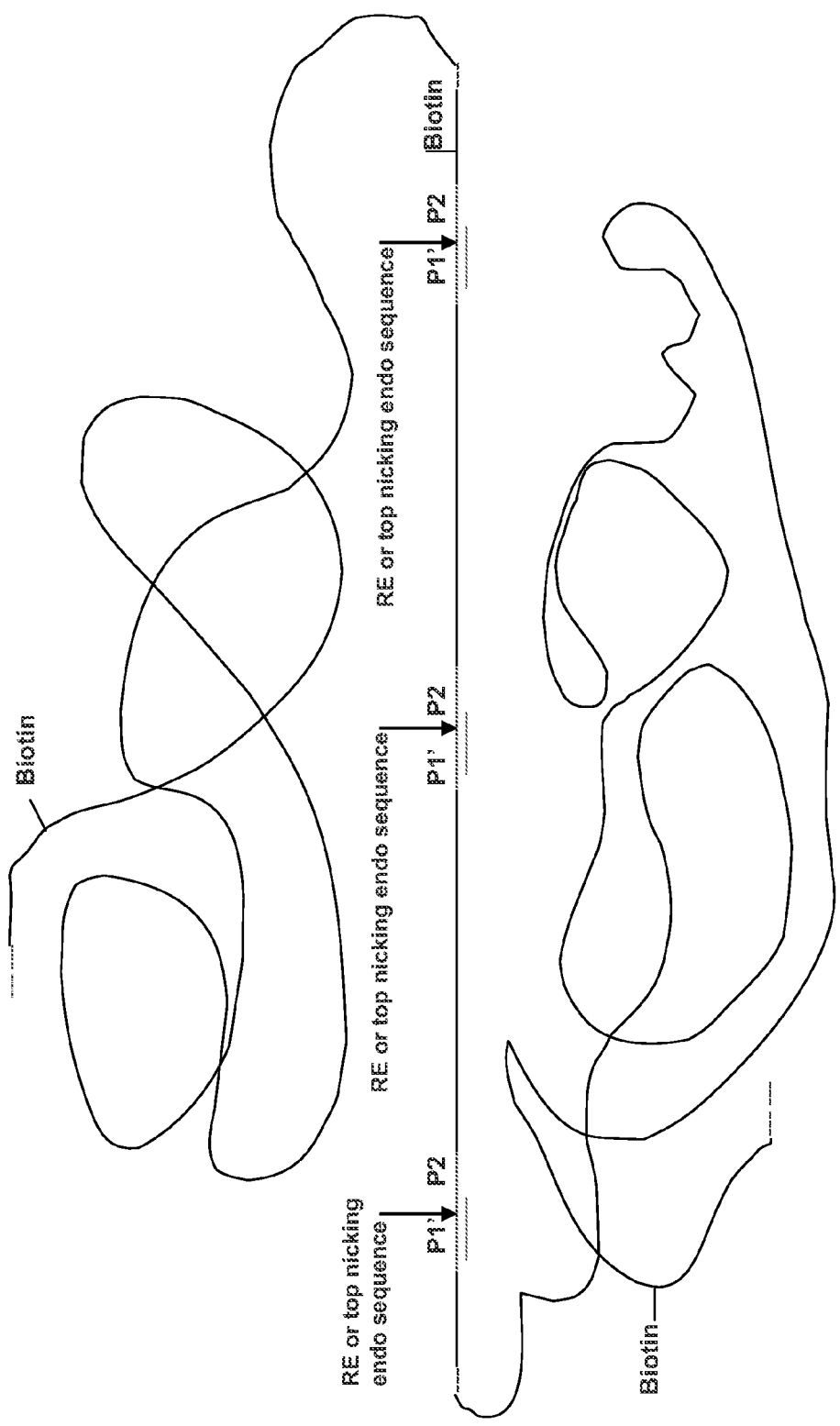
FIG. 6 shows a schematic depiction of hybridization of oligonucleotides having complementary sequences to the site specific endonuclease sequences within the DNA ball thereby providing double stranded structures necessary for DNA cleavage. Cleavage with double stranded DNA specific endonucleases will leave the single stranded target sequences intact.

Prior to amplification of the target DNA molecule, the tandem sequences are cleaved from each other. This is done by hybridizing an oligonucleotide that is complementary to the region of the P1'/P2 sequence, which contain the restriction endonuclease (RE) or top nicking endonuclease recognition sequence (FIG. 6). The double stranded regions are then cleaved by incubation with a site specific nuclease thereby releasing the tandem sequences at the boundary between the P1' and P2 sequences. Many restriction endonucleases are ideally suited for this step because they only cut double stranded structures.

Amplification of the released single stranded tandem sequences occurs by solid-phase assisted PCR. The resulting single stranded sequences are hybridized to the P1 primers on the microbead to provide multiple targets for in-well PCR. Following amplification by PCR, the unattached fragments are washed away and the single stranded fragments on the beads are ready for DNA sequencing. One advantage of the above method is that the amplification of the target sequence only requires P2 primers and other standard PCR ingredients for successful in-well PCR.

Sequencing of the target DNA molecule can be done using a variety of known methods, including Pyrosequencing. Pyrosequencing of the target DNA molecule is conducted by using methods described in US 2009/0286299.

Example II

Loading Microbeads with DNA Balls Using Patterned Polynucleotide Patches on a Chip The following method describes utilizing the surface of a chip that contains patterned polynucleotides for loading microbeads with DNA balls at a desired ratio. Using the described method, single 100-1000 nm active patches are created on a larger microsphere (5-50 μm) such that the active patch can capture a single DNA ball. In this manner, when the microspheres are incubated with DNA balls, the result is that every microsphere has one and only one DNA ball attached to it to allow for later clonal amplification. The seeding of a DNA ball rather than a single library molecule on a microsphere greatly improves the signal to noise in the amplification reaction.

Figure 7:
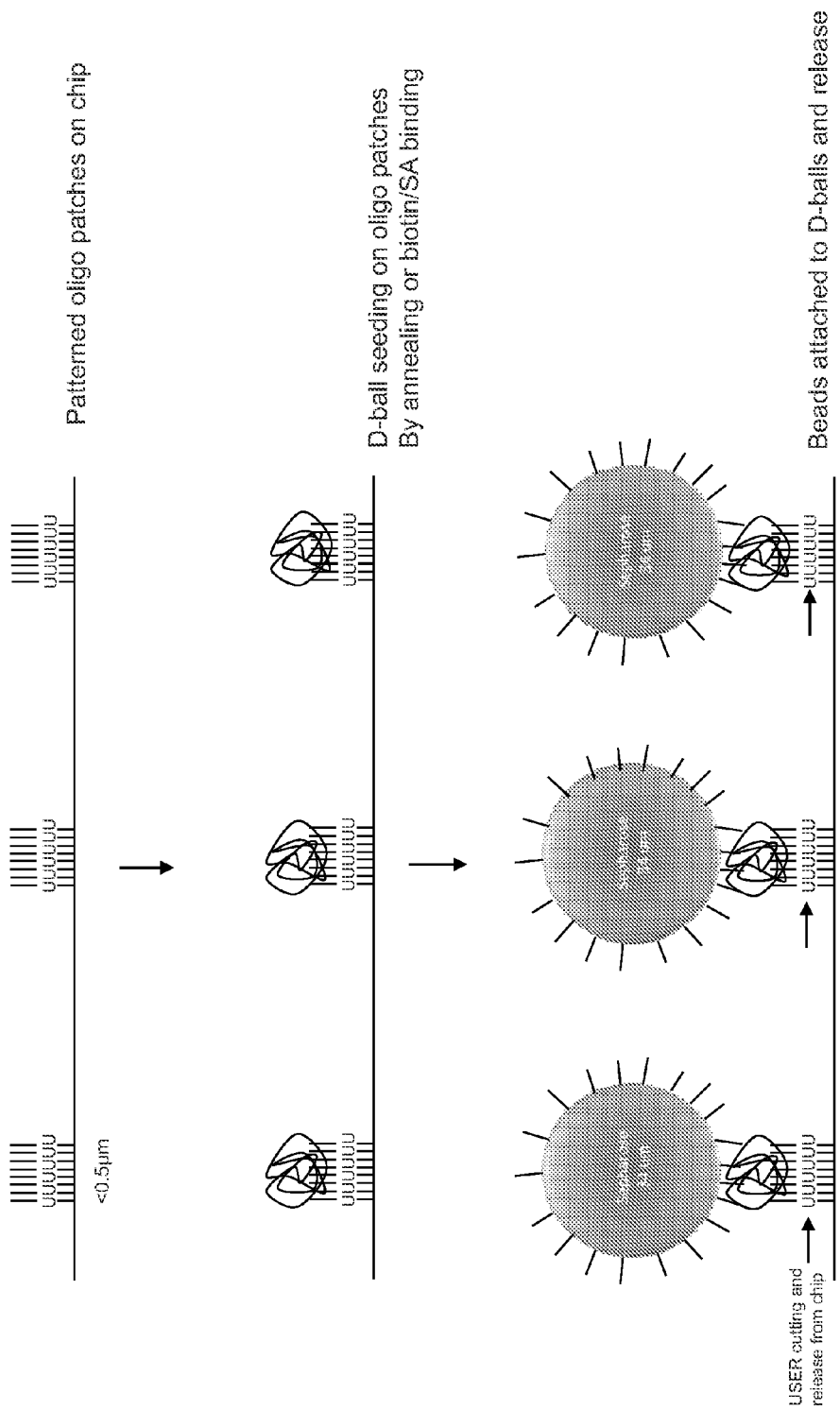
FIG. 7 shows a schematic depiction of a method for fabricating a sepharose microsphere having a single DNA ball.

A chip containing patterned polynucleotides patches is generated by microfabrication lithography. The polynucleotides on the chip contain a cleavable moiety such as uracil to allow for later release from the surface of the chip (FIG. 7). DNA balls containing the desired target nucleic acid molecules are seeded to the surface of the chip by annealing (FIG. 7). Alternatively, DNA balls are generated using the method described in Example I having biotin molecules at the ends or within the ball itself. These DNA balls can be seeded to chips patterned with streptavidin by microfabrication lithography. The patches of polynucleotides or streptavidin are 200-500 nm in size, which sterically allows for attaching a single DNA ball having 100-1000 copies of the target sequence. Once the DNA balls are seeded to the chip, microspheres containing attached polynucleotides are attached to the DNA balls by hybridization to a sequence present in an adapter region. The immobilized balls are then released from the chip by cutting the cleavable moiety attaching the polynucleotides to the chip (FIG. 7). Cutting of the cleavable moiety is performed by Uracil-Specific Excision Reagent (USER available from New England Biolabs, USA).

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method of fabricating a bead having one clonal object comprising:
   (a) providing a bead comprising a plurality of first polynucleotides;
   (b) providing a solid surface comprising a plurality of second polynucleotides patterned into patches on said surface, wherein said second polynucleotides each comprise a cleavable moiety, wherein one clonal object is hybridized to one polynucleotide patch on said surface, and wherein said one clonal object comprises a single tandemly repeated target nucleic acid molecule and a plurality of binding sites;
   (c) hybridizing said first polynucleotides to said plurality of binding sites on said clonal object, thereby forming multiple hybridization events between said clonal object and an immobilized bead on the solid surface, and
   (d) cleaving said second polynucleotides at said cleavable moiety so as to retain said clonal object, thereby fabricating a bead having one clonal object.

2. The method of claim 1, further comprising fabricating multiple copies of said clonal object on a second solid surface comprising:
   (e) providing said second solid surface comprising a plurality of primer polynucleotides;
   (f) hybridizing said clonal object to said primer polynucleotides on said second solid surface, and
   (g) extending said primer polynucleotides to fabricate multiple copies of said clonal object on said second solid surface.

3. The method of claim 1, wherein said first polynucleotides comprise a universal primer sequence.

4. The method of claim 1, wherein said first polynucleotides comprise a target nucleic acid molecule.

5. The method of claim 1, wherein said second polynucleotides comprise a universal primer.

6. The method of claim 1, wherein said solid surface is planar.

7. The method of claim 1, wherein said solid surface comprises regions which are concave or convex.

8. The method of claim 1, wherein said first or second polynucleotides have a length selected from the group consisting of at least 10, 20, 30, 40 and 50 nucleotides.

9. The method of claim 1, wherein said first or second polynucleotides have a length of at least 10 nucleotides and no more than 500 nucleotides.

10. The method of claim 1, wherein said immobilization step is followed by crosslinking said first polynucleotides to said clonal object.

11. The method of claim 10, wherein said crosslinking occurs through a covalent or ionic bond.

12. The method of claim 1, wherein said cleavable moiety is cleavable by a protease, an enzyme or a chemical.

13. The method of claim 1, wherein said cleavable moiety is photocleavable.

14. The method of claim 1, wherein said clonal object is a DNA ball.

15. The method of claim 14, wherein said DNA ball is produced by rolling circle amplification or DNA ligation.

16. The method of claim 1, wherein said clonal object comprises multiple copies of said single tandemly repeated target nucleic acid molecule selected from the group consisting of at least 100, 200, 500, 1000, 2000, 3000, 4000, 5000, 6000, 7000, 8000, 9000 and 10,000 copies.

17. The method of claim 1, wherein said clonal object has a diameter selected from the group consisting of 0.1 μm, 0.2 μm, 0.5 μm, 1 μm, 2 μm, 3 μm, 4 μm and 5 μm.

* * * * *